(12) United States Patent
Silver et al.

(10) Patent No.: US 6,372,511 B1
(45) Date of Patent: *Apr. 16, 2002

(54) SWABBING MEANS AND METHODS OF USE

(75) Inventors: Lawrence Stanley Silver, Hauppauge; Michael Juliano, E. Setauket, both of NY (US)

(73) Assignee: International Food Protection, INC, Bayport, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/370,306

(22) Filed: Aug. 9, 1999

Related U.S. Application Data

(63) Continuation-in-part of application No. 09/228,330, filed on Jan. 11, 1999, now Pat. No. 6,197,254.

(51) Int. Cl.⁷ .......................... G01N 21/76; G01N 21/03
(52) U.S. Cl. ...................... 436/165; 436/169; 436/170; 436/172; 422/52; 422/56; 422/58; 422/59; 422/60; 422/61; 422/82.08; 422/102; 422/940; 435/288.7; 250/361 C
(58) Field of Search .............................. 422/52, 55, 56, 422/58–61, 82.08, 99, 100, 102, 939, 940; 436/164, 165, 169, 170, 172, 180; 435/288.7; 250/361 C

(56) References Cited

U.S. PATENT DOCUMENTS

| | | | |
|---|---|---|---|
| 4,672,039 A | 6/1987 | Lundblom | 435/291 |
| 5,188,965 A | 2/1993 | Wannlund | 436/165 |
| 5,565,360 A | 10/1996 | Lapota et al. | 435/286 |
| 5,580,785 A | 12/1996 | Stiffey et al. | 435/288 |
| 5,624,810 A * | 4/1997 | Miller et al. | 435/8 |
| 5,783,399 A | 7/1998 | Childs et al. | 435/7.2 |
| 5,811,251 A | 9/1998 | Hirose et al. | 435/8 |
| 5,827,675 A * | 10/1998 | Skiffington et al. | 435/8 |
| 5,905,029 A * | 5/1999 | Andreotti et al. | 435/8 |
| 5,980,828 A * | 11/1999 | McClintock et al. | 422/58 |
| 6,043,047 A * | 3/2000 | Foote et al. | 435/21 |
| 6,140,136 A * | 10/2000 | Lee | 436/518 |
| 6,197,254 B1 * | 3/2001 | Silver et al. | 422/52 |

FOREIGN PATENT DOCUMENTS

| | | |
|---|---|---|
| EP | 0038134 B1 | 7/1985 |
| EP | 0717840 B1 | 4/1998 |
| WO | 98/49544 * | 11/1998 |

* cited by examiner

Primary Examiner—Maureen M. Wallenhorst
(74) Attorney, Agent, or Firm—Island Patent; F. S. Tierno

(57) ABSTRACT

Swabbing structures and methods of use are provided that enable a test surface to be swabbed, and subsequently facilitate a quantitative determination of the quantities of analyte collected from the test surface. The swabbing structures include a pre-wetted swabbing pad having a first surface structured for contacting and suitably swabbing the test surface to collect the analyte. Dried reagents are then brought into pressure contact with the swabbing pad, within a light-tight environment, to commence an assaying reaction. The assaying reaction may produce low level luminescent emissions that are detected and quantified to indicate the quantity or volume of analyte collected.

13 Claims, 21 Drawing Sheets

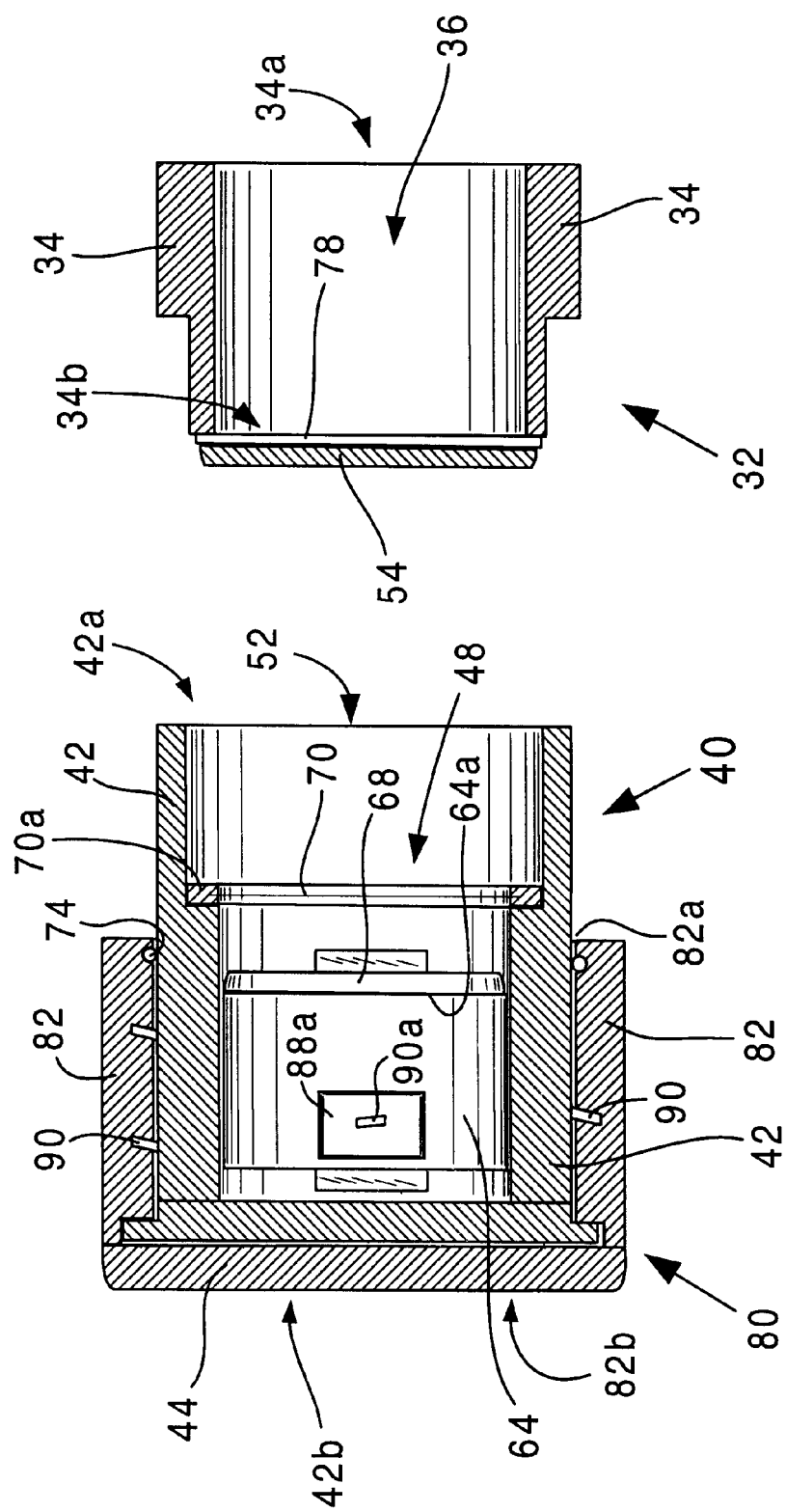

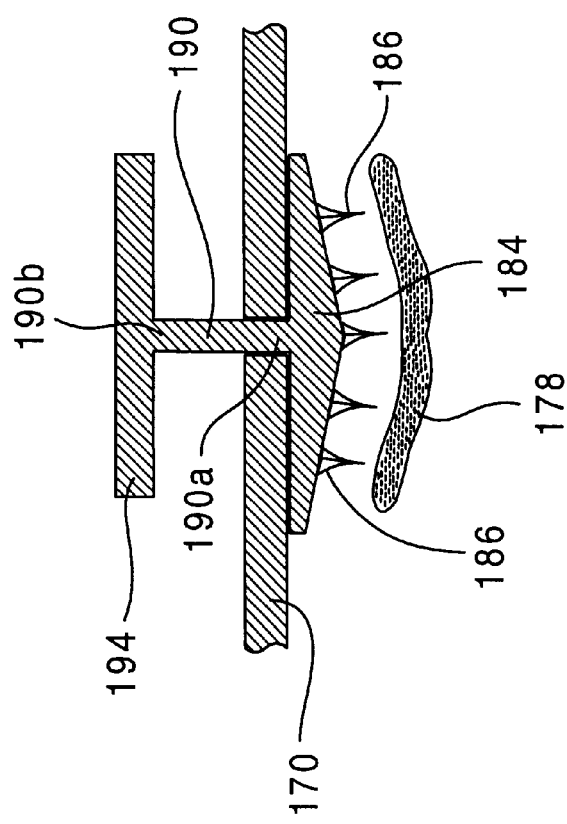
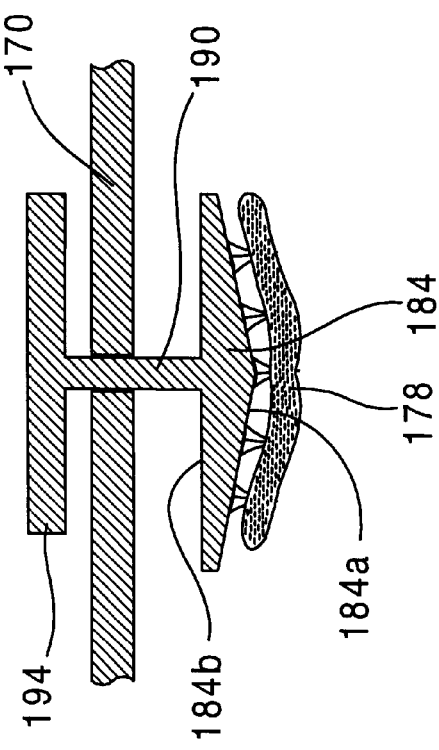
FIG. 9B
FIG. 9C

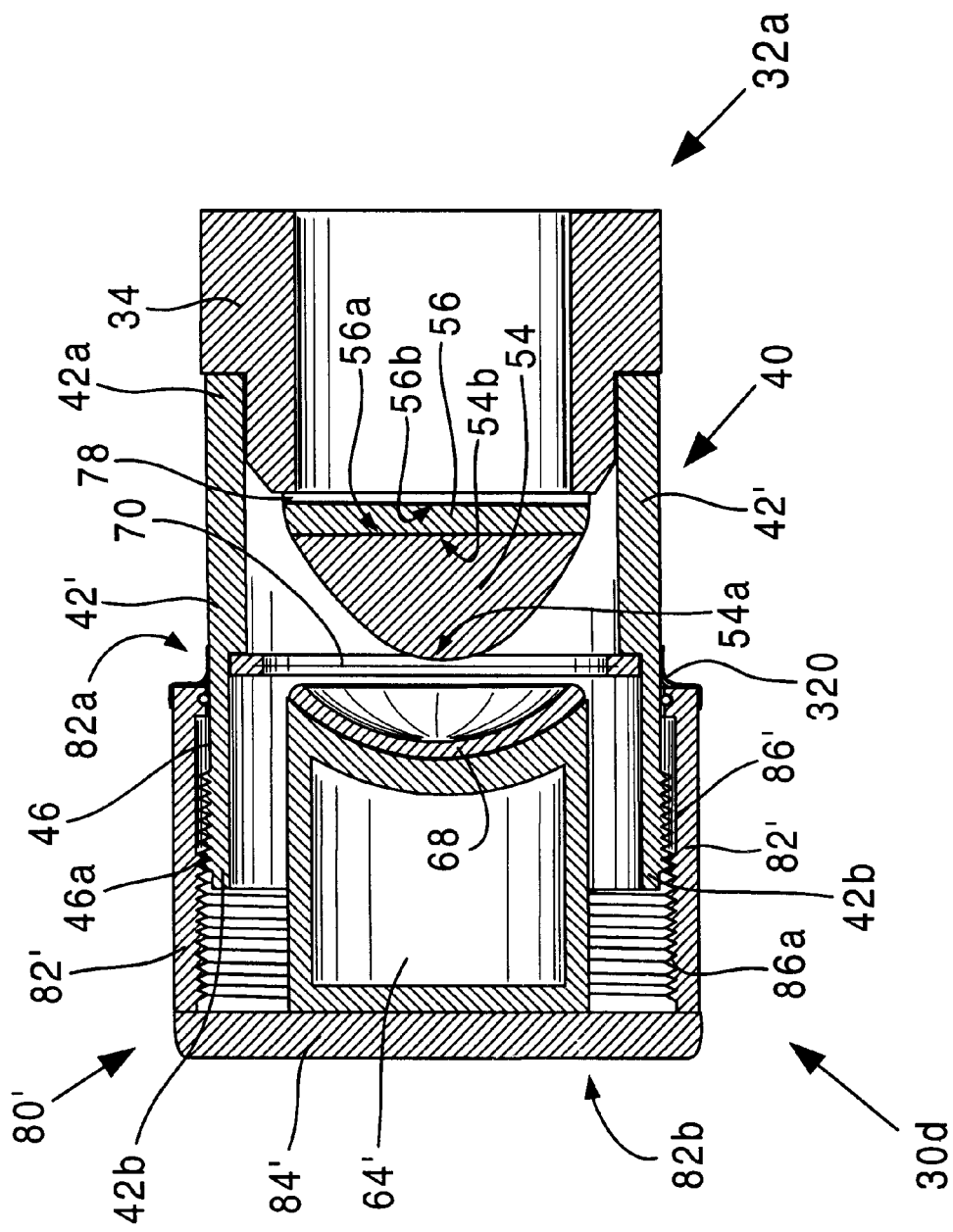

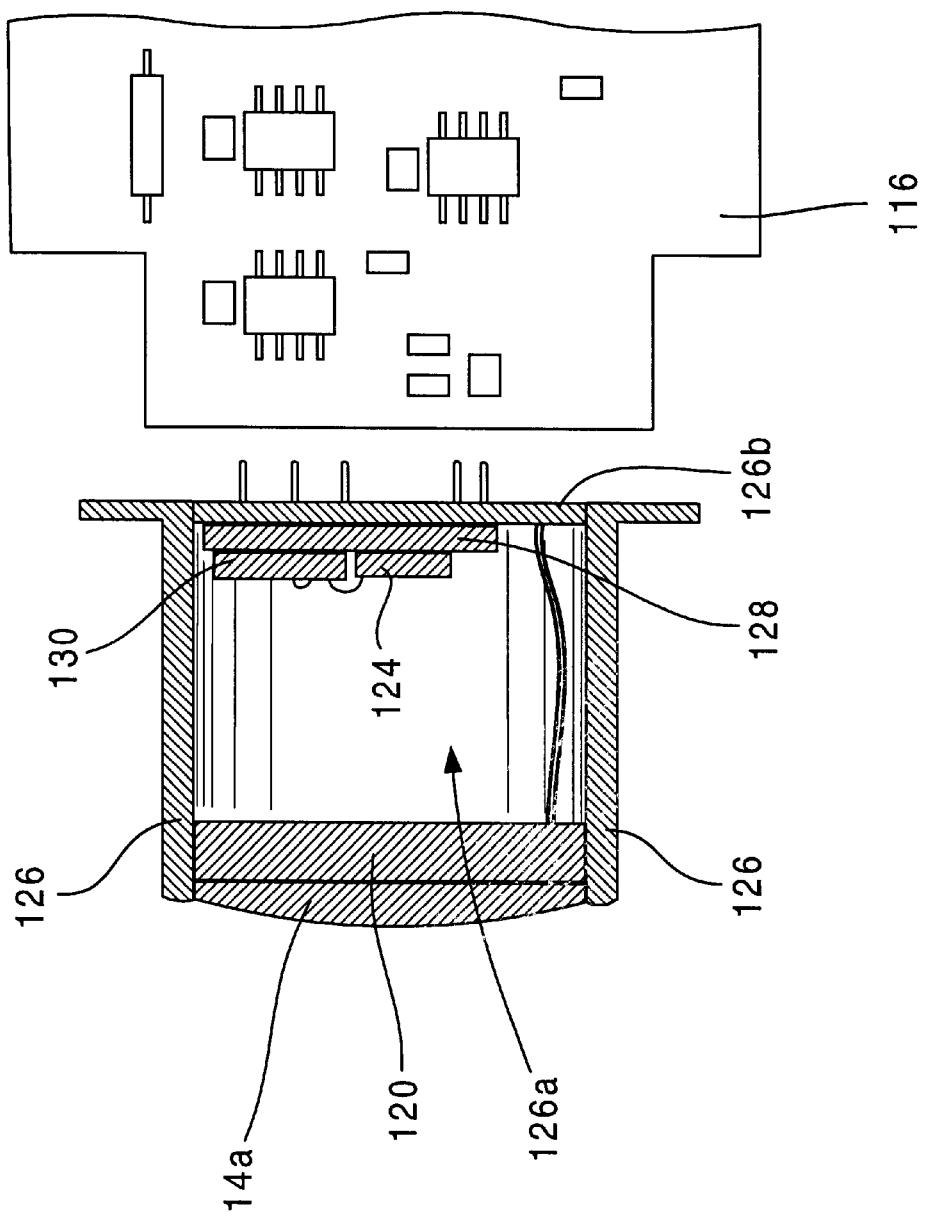

SWABBING MEANS AND METHODS OF USE

CROSS REFERENCE TO RELATED APPLICATION

The subject matter provided herein represents a continuation-in-part of application Ser. No. 09/228,330 filed on Jan 11, 1999, now U.S. Pat. No. 6,197,254, issued on Mar. 6, 2001, and hereby incorporated by reference.

BACKGROUND OF THE INVENTION

1. Field of the Invention

The present invention relates generally to swabbing structures and methods of use for assaying purposes. More particularly, the invention relates swabbing structures for collecting analyte from a test surface and conducting an assay in a light-tight environment to efficiently detect and quantify low level luminescent emissions, which are proportional to the volume of analyte collected from the test surface.

2. Description of the Prior Art

Hitherto, a number of techniques and arrangements have been proposed that employ 'luciferase-luciferin reactions' to assay and quantify a specimen or a volume of analyte. As is well known, luciferase-luciferin reactions involve the measurement of adenosine triphosphate (ATP), a material central to metabolism in virtually all living cells. As ATP is necessary for all living organisms to function, it serves as an excellent marker to indicate the presence of living matter (e.g., bacterial and other microbial matter). Accordingly, if one can ascertain with a reasonable accuracy a quantity of ATP present in a sample or specimen, either through direct or indirect measurement, one can make a determination of the quantity of microbes, microbial matter, or more generally the amount of 'analyte' present. A most preferred indirect method of measuring and quantifying a volume of analyte is by determining the levels of ATP present by employing a luciferase-luciferin assaying reaction. A properly conducted luciferase-luciferin reaction will produce detectable and measurable levels of luminescent emissions—even with relatively small quantities of analyte (e.g., down to 1 femtomole, or fm). However, it must be understood that the level of luminescent emissions generated by such assaying reactions may be quite low. For example, such levels of emissions may be as low as a fraction of a pico-watt. The measurement of levels of emission this low necessitates sensitive, efficient, and accurate detecting and measuring systems that include low noise and generally a number of specialized components.

There are many assaying and 'luminometer' systems known and available that employ photomultiplier tubes (PMTs) and cooled charge-coupled devices (CCDs) to measure low level emissions produced by bioluminescent and chemiluminescent assaying reactions. However, when considering PMT based devices, their cost is relatively high, and they may be easily damaged by shock and vibration. Further, as these devices require a high voltage supply and temperature stabilization for proper calibrated operation, they are rarely employed in low cost, low power, highly portable instruments. CCD based devices can also be expensive, especially when structured to provide the necessary sensitivity. In addition, they are generally considered to have dark noise levels that are too high for low level luminescent emission measurements, say at a 'sub' pico-watt level or less. As a consequence, when CCD devices are employed, they are almost always operated at a cooled, controlled temperature (which is generally well below the ambient temperature).

Alternative and generally low cost photo-sensing devices may be found in a number of solid-state (semiconductor) photodetectors including avalanche photodiodes, silicon-carbide photodiodes, PIN photodiodes, etc. Avalanche photodiodes, which are typically operated in a photo-conductive mode, have excellent bandwidth characteristics and good sensitivity. However, as with many CCD devices, they exhibit a 'dark current' that is generally considered too high for very low level luminescent measurements. Avalanche-photodiodes are also more expensive than other semi-conductor photodiodes, and as with PMTs, are often cooled to reduce their dark current noise levels. Other solid-state photodiodes, for example Silicon-carbide photodiodes, are not appropriate for ATP assay measurements as they have a peak sensitivity in the ultraviolet spectrum, say in the range of 200 to 380 nano-meters. PIN photodiode detectors have generally not been considered to be sensitive enough to use in low level ATP assaying luminometers. Indeed, it has generally been accepted that semiconductor diodes, including PIN diodes, are simply not suitable for such applications. This is indicated by the fact that photomultiplier tube (PMT) devices, as well as CCD based systems, have been used almost exclusively in luminometers to measure low level luminescent emissions.

Assaying arrangements that employ bioluminescent (ATP) assaying reactions to produce low levels of luminescent emissions require a means to collect a specimen or sample. Once a sample has been collected (say with a cotton tipped swab), the sample is assayed by exposure to suitable reagents and enzymes to cause the luminescent emissions-producing reaction to occur. The art provides many examples of luminometer apparatus that are employable in a lab or testing facility to measure emissions of an assaying reaction. However, these assaying arrangements are not provided in self-contained and highly portable architectures structured for the "efficient detecting" of such low-levels of luminescent emissions. Therefore, such systems have not been usable in the field, for example, if a cleanliness or hygiene inspection is being conducted in a hospital operating room or in a restaurant's kitchen. In addition, known swabbing structures and associated assaying arrangements do not provide simple, self-contained, and efficient structures to collect a sample of analyte, initiate an assaying reaction in a light-tight environment, and sense and quantify the low levels of luminescent emissions associated therewith.

Accordingly, skilled persons will recognize the need for improved low level, self-contained and highly portable assaying apparatus, and associated (efficient) swabbing arrangements and structures. A most preferred apparatus and or swabbing structure would enable specimens to be collected, provide a suitable light-tight assaying environment (i.e., enclosure), include required chemical and biological materials to initiate the assaying reaction, and further enable or; support the quantifying of the low level luminescent emissions produced by the assaying reaction. A full understanding of the present invention, including an understanding of a number of capabilities, characteristics, and associated novel features, will result from a careful review of the description and figures of the embodiments provided herein. Attention is called to the fact, however, that the drawings and descriptions are illustrative only. Variations and alternate embodiments are contemplated as being part of the invention, limited only by the scope of the appended claims.

SUMMARY OF THE INVENTION

In accordance with the present invention swabbing structures, and methods of use, are provided for collecting analyte from a test surface and supporting a quantitative determination of the presence of the collected analyte. A preferred swabbing structure is configured to enable analyte to be collected upon a first surface of the swabbing pad, and subsequently detect and quantify low level luminescent emissions from (a vantage point of) a second surface or side of the swabbing pad.

In addition, preferred embodiments of the swabbing structure include a pre-wetted swabbing pad having the first surface and the second surface. Although the swabbing pad may be substantially flattened, other shapes including 'swab shaped' and 'wedge shaped' are also contemplated. Regardless of the actual shape of the (first surface of the) swabbing pad, the first surface is configured for contacting the test surface to collect available analyte located thereupon. A substantially flattened, highly porous, support and reading pad may also be provided having a first surface fixed to the second surface of the swabbing pad. The first surface of the support and reading pad, therefore, is substantially superposed by the second surface of the swabbing pad, with the support and reading pad acting, at least in part, as a physical base or support for the swabbing pad. A second surface of the support and reading pad is contemplated to provide an efficient vantage point from which to detect and quantify the low level luminescent emissions.

In addition to the swabbing pad, and the support and reading pad, a means to support the support and reading pad, and or the swabbing pad is included to enable the swabbing of the test surface and subsequently facilitate the detecting, in a light-tight environment, of any low level luminescent emissions. The emissions may be detected from the second side of the swabbing pad, or if included, a second side of support and reading pad. A movable structure is further included having fixed thereto a porous pad, or an equivalent structure. The porous pad is impregnated with suitable dried reagents that may be delivered to the swabbing pad, and other pads, when the movable structure is moved to bring the porous pad into pressure contact with the first surface of the pre-wetted swabbing pad (within the light-tight environment). As will be discussed in great detail below, the pressure contacting of the porous pad and the swabbing pad causes at least a partial compressing of the swabbing pad, which in turn causes the wetting, activating, and drawing of the (dried) reagents of the porous pad into the swabbing pad (and possibly other included absorbent, porous pads and structures). If suitable quantities of analyte have been collected by the swabbing of the test surface, an assaying reaction results that produces the low level luminescent emissions. Importantly, due to the 'reflective porosity' of structures such as the swabbing pad, and the support and reading pad, emissions produced upon or near these structures, may be efficiently sensed by placing a photo detection means (e.g., a suitable photodiode) in a suitable position proximate to the second surface of the swabbing pad, or the support and reading pad, if included.

The invention further discloses preferred methods for swabbing a test surface in order to collect and quantitatively indicate the presence of an analyte. The methods commence with the swabbing of the test surface with a pre-wetted swabbing pad. As discussed, a first surface of the swabbing pad is suitably shaped and configured for contacting the test surface to collect any available analyte. Next, the first surface of the swabbing pad is brought into pressure contact with suitable dried reagents in a light-tight environment, possibly causing the detectable low level luminescent reaction (if sufficient analyte has been collected). The efficient detecting and quantifying of the low level luminescent emissions may be made by a suitable luminometer or an equivalent instrument. Importantly, the most preferred embodiments of the methods of the present invention, provide for the collecting of analyte upon the first surface of a swabbing pad with reading and detecting of luminescent emissions being made from a second side (or surface) of the swabbing pad (possibly via the support and reading pad).

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows:

FIGS. 5A, 5B, and 5C, provide sectional side views of a first embodiment of a detector cap assembly of the present invention.

FIGS. 9B and 9C illustrate an embodiment of a perforation means in a first non-actuated position. (FIG. 9B) and a second actuated position (FIG. 9C).

FIGS. 10A and 10B illustrate sectional views of another preferred embodiment of a detector cap assembly.

FIGS. 17A and 17B illustrate preferred embodiments of photodiode detection devices that may be employed with the photodiode detector head assembly and luminometer of the invention.

PARTIAL LIST OF REFERENCE NUMERALS

Figure 1:
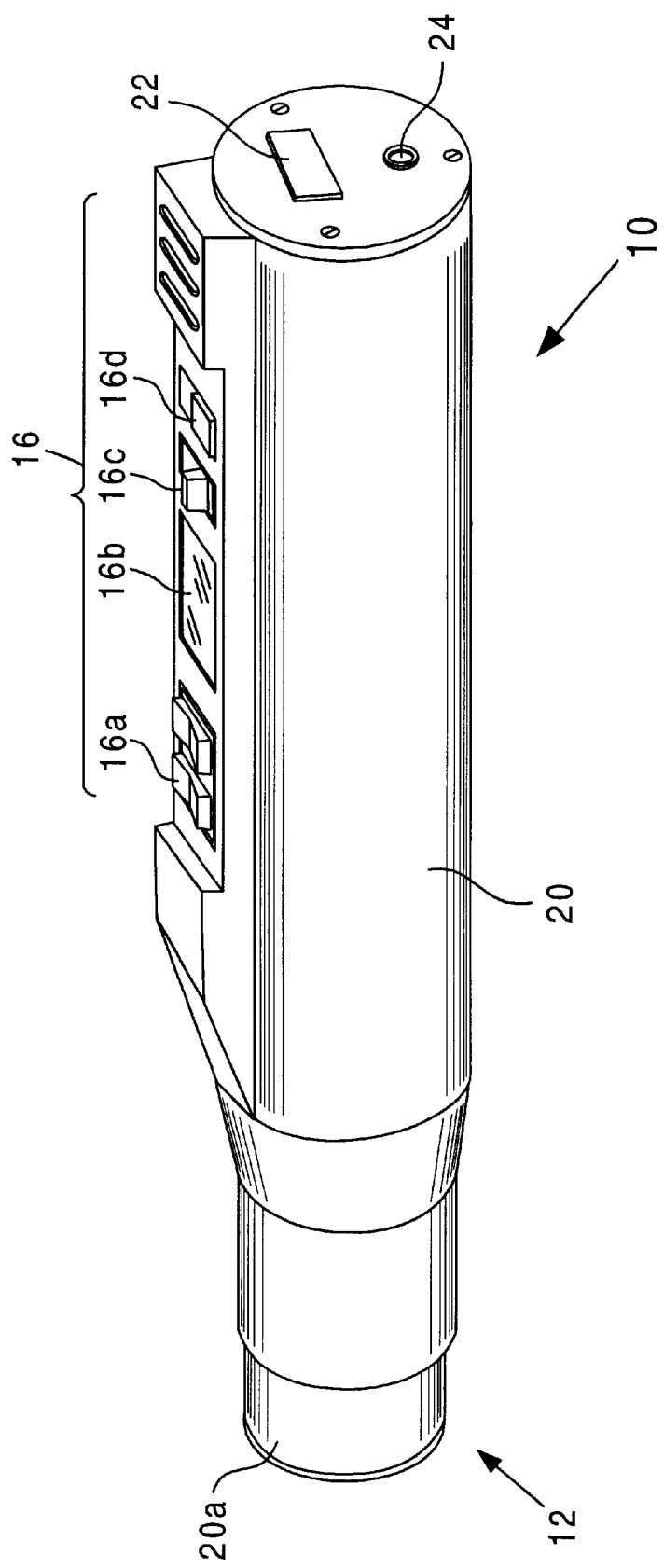
FIG. 1 illustrates a perspective view of an embodiment of a hand holdable luminometer in accordance with the present invention.

| | |
|---|---|
| 10 | luminometer |
| 12 | photodiode detector head assembly |
| 14 | transparent or optical window |
| 16 | user interface (including 16a, 16b, 16c, 16d) |
| 17 | current signal |
| 18 | electrical signal |
| 20 | housing |
| 20a | detector head housing |
| 30 | detector cap assembly |
| 32 | first portion (of detector cap assembly 30) |
| 34 | wall structure of first portion |
| 34a | first opening of first portion |
| 34b | second opening of first portion |
| 36 | internal cavity of first portion |
| 40,40' | second portion (of detector cap assembly 30) |
| 42,42' | wall structure of second portion |
| 42a | first end of second portion |
| 42b | second end of second portion |
| 44,44' | top (surface) of second portion |
| 46 | outer surface of wall structure 42' |
| 46a | threaded portion of outer surface |
| 48 | internal chamber of second portion |
| 52 | opening to internal chamber of the second portion |
| 54 | swabbing pad |
| 54a | first (swabbing) surface (of swabbing pad 54) |
| 54b | second surface (of swabbing pad 54) |
| 56 | support and reading pad |
| 64,64' | movable structure |
| 64a | surface of movable structure |
| 68 | porous pad |
| 70 | first barrier, or sealing means |
| 70a | support ring for first barrier |
| 78 | second barrier |
| 79 | (small) pocket |
| 80,80' | cap-like portion |
| 82,82' | wall structure of cap-like portion |
| 82a | first (open) end of cap-like portion |
| 82b | second (closed) end of cap-like portion |
| 84,84' | top surface of cap-like portion |
| 86,86' | interior surface of wall structure |
| 86a | threaded portion of interior surface of wall structure |
| 88 | slot in wall structure of second portion |
| 88a | raised block |
| 90 | spiral groove |
| 90a | follower tab |
| 116 | circuit board (of luminometer 10/10a) |
| 118 | digital values (from analog-to-digital module) |
| 120 | electronic shutter |
| 124 | photodiode or semiconductor photodetector |
| 124a | PIN photodiode |
| 126 | photodetector package |
| 126a | chamber within photodetector package |
| 126b | base of photodetector package |
| 128 | thermoelectric cooler |
| 130 | pre-amplifier |
| 140 | second portion (alternate embodiment) |
| 142 | wall structure (of alternate embodiment) |
| 142a | bottom end (of wall structure 142) |
| 142b | top end (of wall structure 142) |
| 142aa | bottom opening |
| 142bb | top opening |
| 146 | cavity of second portion |
| 160 | first partition wall |
| 162 | hole(s) in first partition wall |
| 170 | second partition wall |
| 172 | hole in second partition wall |
| 176 | pellet(s) of dried reagent |
| 178 | fluid holding envelope |
| 180 | chamber (between first and second walls) |

-continued

PARTIAL LIST OF REFERENCE NUMERALS

| | |
|---|---|
| 184 | perforation disk |
| 184a | first surface of perforation disk |
| 184b | second surface of perforation disk |
| 190 | shaft |
| 190a | first end of shaft |
| 190b | second end of shaft |
| 196 | spring, bias means |
| 198 | lid |
| 200 | signal conditioning module (means) |
| 210 | filter and amplification module |
| 220 | integrator |
| 230 | analog-to-digital module |
| 280 | power regulator |
| 300 | computer |
| 320 | safety locking means |
| 400 | result or results |

DETAILED DESCRIPTION OF THE INVENTION

It is important to establish the definition of a number of terms and expressions that will be used throughout this disclosure. The terms 'coupled', 'operatively coupled', and equivalents, are to be assumed to indicate the functional and or operational connection of one device or module to another, either directly or with one or more other devices or modules interposed. A functional or operational connection being required to deliver, receive, or more generally enable information including signals, data values, commands, etc., to be exchanged between one or more respective items, devices, or modules. Accordingly, the terms coupled, operatively coupled, and the like, are to be considered synonymous, and somewhat broadly defined. The terms 'signal' and 'electrical signal', which are well known to skilled persons, may be provided by at least one suitable current and or voltage signal. The term 'luminometer', which is used extensively through out this disclosure, defines a means to measure low levels of luminescent emissions. Importantly, the luminometer of the present invention is embodied to provide a very portable, hand holdable or belt/waist supported, self-contained instrument that may be employed to measure said low level emissions when, for example, an assay is being conducted. The expression 'low level luminescent emissions', and similar expressions, are to be assumed to indicate levels of emissions typified by, for example, a luciferase-luciferin type of bioluminescent assaying reaction. Such an assaying reaction, as well as other known reactions, may produce a correspondingly low level emission, say for example, in the range of one-hundredth of a pico-watt to tenths of a pico-watt. Further, such emissions are preferably within the visible light spectrum. The term 'analyte' is to be understood to encompass small microbes including, but not limited to, bacteria, viruses, other chemical moieties, and the like. Further, 'analyte' may be assumed to be singular or plural, as appropriate for the context in which it is used. The term 'wall structure' will be used primarily to refer to side walls of several portions of a detector cap assembly of the present invention. It should be understood that the term wall structure may be extended to include a top or end wall of a respective item being described, as determined by the context in which the term (wall structure) is applied. Other important terms and definitions will be provided, as they are needed, to properly and concisely define the present invention and its associated novel characteristics and features.

Figure 2:
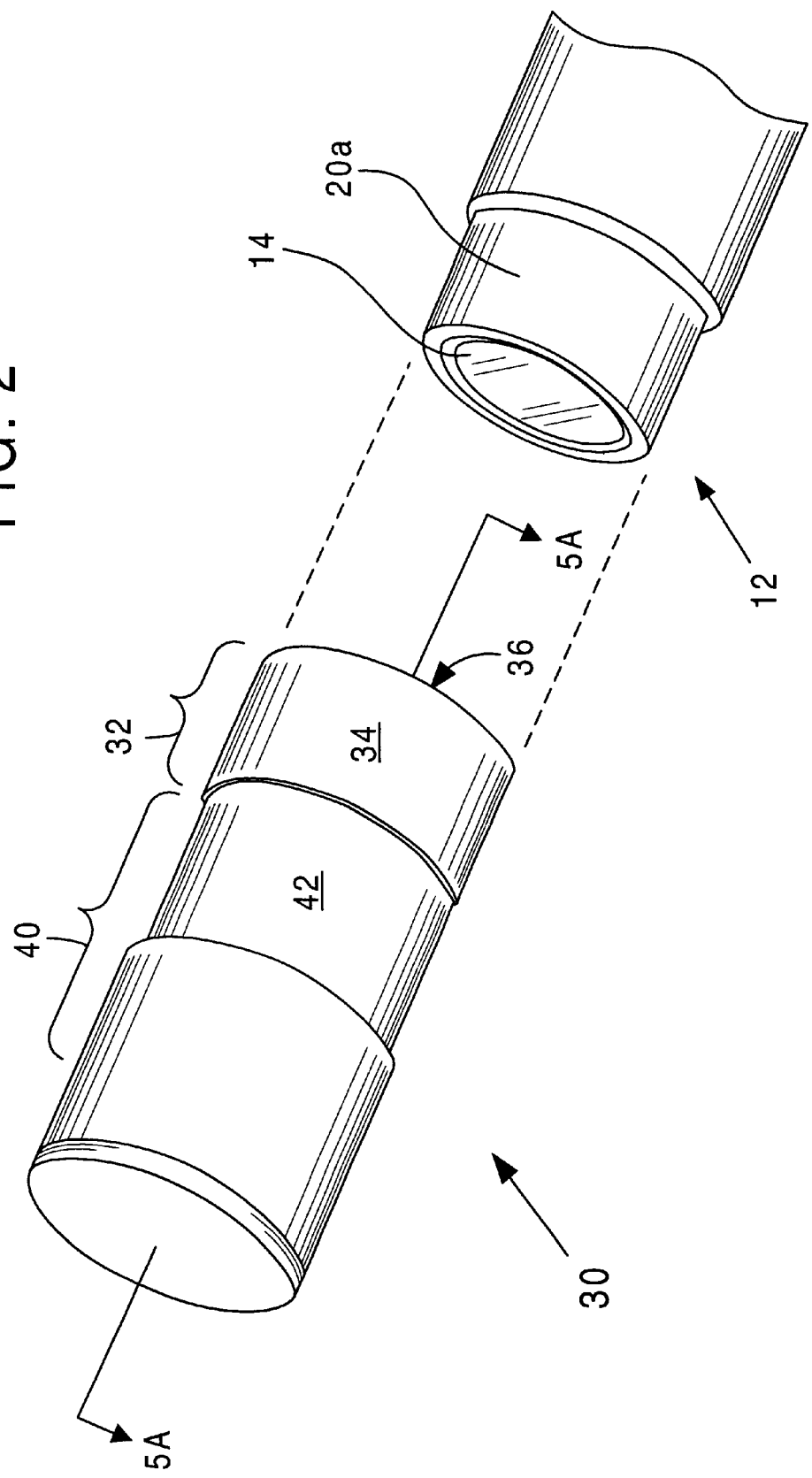
FIG. 2 depicts a perspective view of an embodiment of a detector cap assembly and a photodiode detector head assembly of the invention.

Referring now to FIG. 1, there is illustrated a therein a hand-holdable self-contained luminometer 10 for use in detecting and quantifying low levels of luminescent emissions. As can be seen, the luminometer 10 includes a photodiode detector head assembly 12 structured with a window 14. The transparent window 14, which is best seen in FIG. 2, enables the luminescent emissions to be detected by a suitable 'photo detection means' included within the photodiode detector head assembly 12. It should be noted that the photodiode detector head assembly 12 may be housed within the detector head housing 20a portion of the housing 20. However, many suitable arrangements of the housing 20, and the detector head housing 20a are possible. For example, an alternate arrangement contemplated may provide for the detector head assembly 20a to be recessed within housing 20 (not illustrated). As such, a detector head assembly 20a, which is a male-type structure, may be converted to an equivalent arrangement possibly having a 'detector receptacle' or 'detector well', which would be a female-type of structure.

Figure 16:
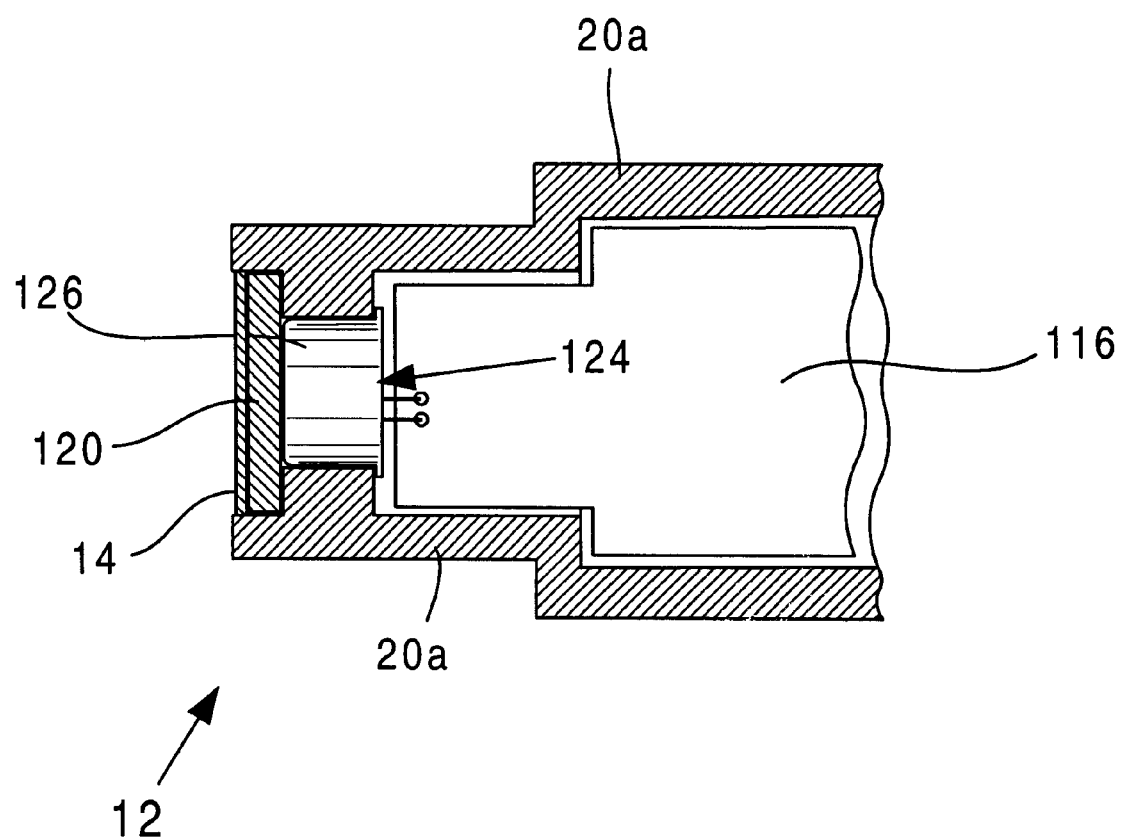
FIG. 16 provides a sectional side view of an embodiment of a photodiode detector head assembly.

The photodiode detector head assembly 12 provides at least one electrical signal representative of the level of detected luminescent emissions. That is, one or more electrical signals are provided that are preferably proportional to the level of incident luminescent emissions passing through the window 14 and detected by the photodiode detector head assembly 12 (as best seen in FIGS. 2 and 16).

As will be discussed in greater detail below, the hand holdable housing 20 of the preferred embodiment is provided to house required electronic modules and components that may include a signal conditioning module and al computer. In order to be easily held and conveniently used to collect and assay specimens, a preferred elongated embodiment of the housing 20 has been depicted in FIG. 1. As shown, this embodiment is arranged with a narrowed detector head housing portion 20a having the photodiode detector head assembly 12 mounted therein. Accordingly, the embodiment of the luminometer 10 illustrated may be termed 'pen-like' or 'marker shaped'. As indicated above, other embodiments, possibly having alternate swabbing structures that are insertable into a suitable detector head receptacle (not illustrated) are contemplated as being within the scope of the present invention.

Also provided with luminometer 10 is a user interface 16, which may be composed of items including rocker switches 16a, slide switches 16c, a display mean 16b, and or other well known user interface components. The user interface 16 is provided to, among other things, enable information including a result to be delivered to a user or operator. The user interface 16 will be discussed further below when referring to FIGS. 13–15.

Turning now to FIG. 2, there is depicted therein an embodiment of a detector cap assembly 30 of the present invention. The detector cap assembly 30 is comprised of a first portion 32 and a second portion 40. The first portion 32 is configured having a wall structure 34 providing an internal cavity 36. As can be clearly seen in FIG. 5A (for example) the wall structure 34, which is preferably cylindrical, defines a first opening 34a and a second opening 34b. The first opening 34a and wall structure 34 of the first portion 32 are structured to enable the first portion 32 to be removably fixed over the photodiode detector head assembly 12 in a light-tight manner, as can be clearly seen in FIGS. 3 and 5A. The expression 'light-tight manner' is intended to mean that the first portion 32 will mate to the photodiode detector head assembly 12 so as to only enable luminescent emissions passing through the second opening 34b of the first portion 32 to be incident upon the window 14 (and a photodiode detection means situated behind said window). In a most preferred embodiment the first portion 32 will preferably install over (in a removably fixed fashion) the photodiode detector head assembly 12 such that at least a portion of the photodiode detector head assembly substantially fills the cavity 36 of the first portion 32 so as to position the window 14 of the photodiode detector head assembly 12 (as shown in FIGS. 6A) in close proximity to the second opening 34b of the first portion. Accordingly, this arrangement will minimize the distance between the photo detection means and the swabbing pad 54, as can be seen in FIG. 6A. This arrangement, wherein the distance is minimized, enables the low level luminescent emissions in accordance with the present invention to be readily detected when generated by an assaying reaction that is occurring on, within, or adjacent to the swabbing pad 54. As such, the minimal distance between the location of the reaction supporting porous pads (such as swabbing pad 54 and or porous pad 68) and the photodiode detection means results in 'efficient detecting' or an 'efficient detection' arrangement. In fact, a preferred embodiment of a swabbing structure of the present invention enables an analyte to be collected upon a first swabbing surface 54a, with luminescent emissions detected by a detection means positioned on (i.e., very near or adjacent to) a second surface 54b of the swabbing pad 54. This aspect of the invention will be discussed in great detail below.

Figure 3:
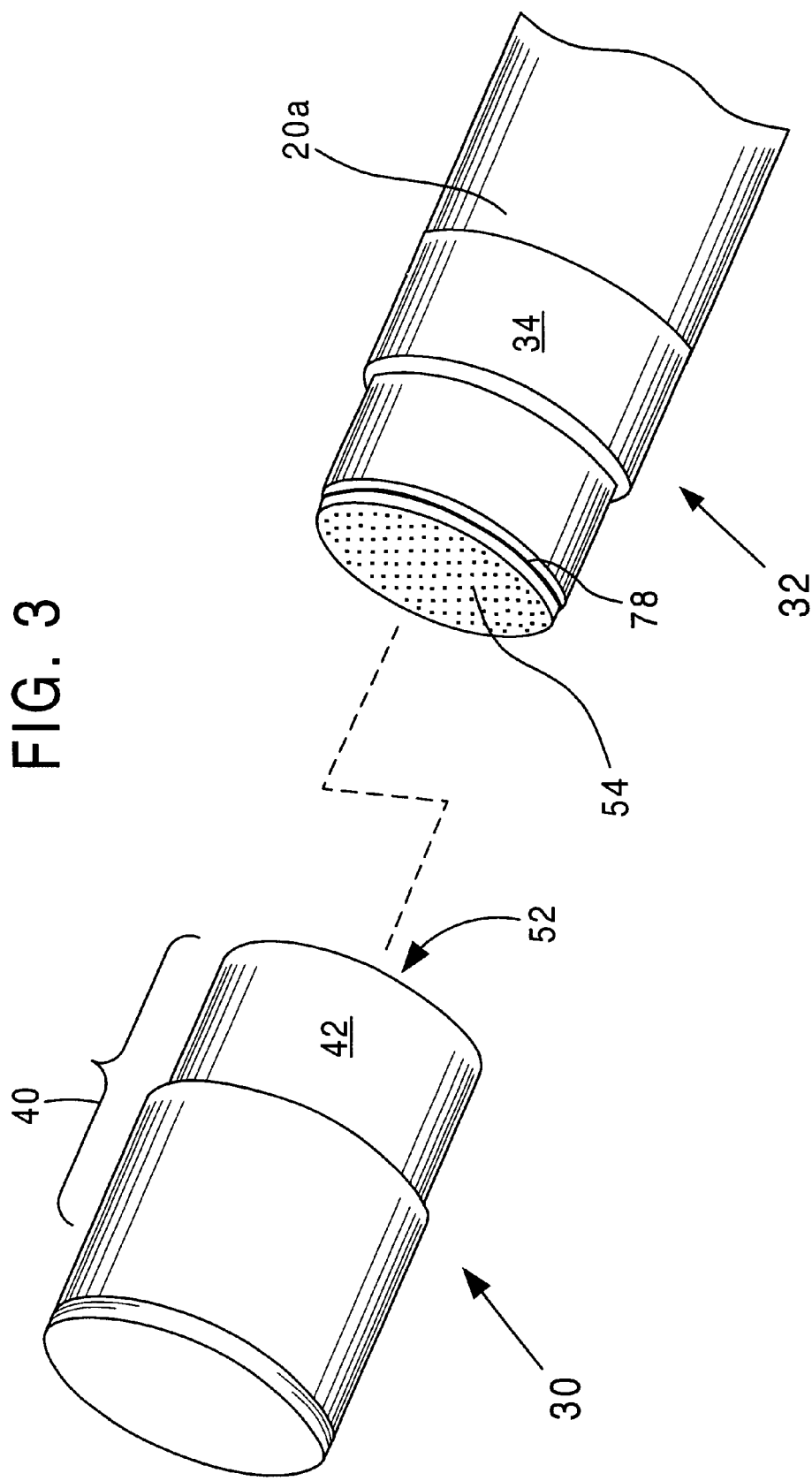
FIG. 3 provides a perspective view of the detector cap assembly of FIG. 2 with a first swabbing portion installed over a photodiode detector head assembly of the luminometer and ready to be used for swabbing and analyte collection.
Figure 4:
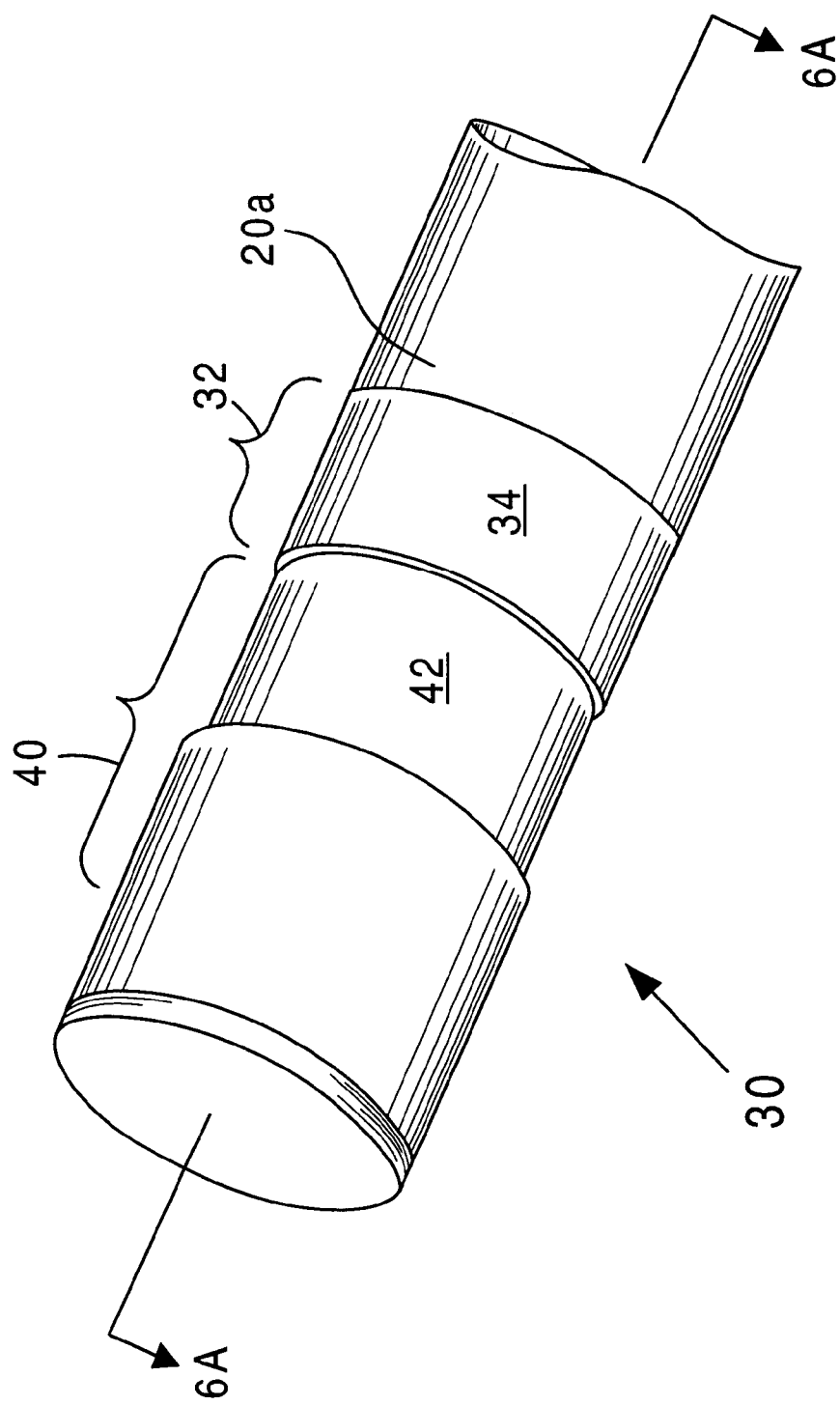
FIG. 4 illustrates the detector cap assembly of FIGS. 2 and 3, reassembled, housing a swabbing pad and related structures in an interior light-tight environment, possibly ready to be activated to conduct an assay.

Referring again to FIG. 2, it may be assumed that the detector cap assembly 30 may have been removed from a sealed, possible sterile, packaging arrangement (not explicitly shown). Once removed from the packaging arrangement, the detector cap assembly 30 may be installed over the photodiode detector head assembly 12 in the light-tight manner, as shown in FIG. 4. Next, the second portion 40 is separated from the first portion 32. It may be noted that the second portion 40 may be coupled to the first portion 32 by a tether (not shown), or alternately, a hinge employed with a suitably structured first portion and second portion to enable the second portion to uncap the first portion and swing out of the way to expose the swabbing pad 54 and a first swabbing surface 54a. As depicted in FIG. 3, the swabbing pad 54 is now exposed and available for swabbing of selected surfaces to, for example, collect microbial matter (i.e., the analyte to be investigated) upon the first swabbing surface. In the embodiments of the swabbing pads 54 illustrated in FIGS. 3 through 9C, the swabbing pad 54 is provided as a substantially flattened and pre-wetted "bibulous" surface that is fixed to the first portion 32 of the detector cap assembly 30 and arranged to substantially cover the second opening 34b thereof. It must however be noted that the swabbing pad 54 may be provided in a large variety of shapes, as can be seen in FIGS. 10A, 10B, 11A, and 11B. As shown therein, a first surface 54a of the depicted swabbing pads 54 may not be flat. Indeed, when it is desired to swab and collect analyte from a crevice or along a curved, angled, or folded surface, a swabbing pad having a shape similar to that illustrated in FIG. 11B may be most preferable. Importantly, as shown, the swabbing pad 54 may most preferably be structured with a substantially flattened second surface 54b, which is typically positioned superposed over and essentially abutting the window 14 of the photodiode detector head assembly 12 (when the first portion 32 is removably fixed over the photodiode detector head assembly 12 in the light-tight manner). Once the selected surface has been swabbed to collect analyte, the second portion 40 is re-installed over the first portion 32, as depicted in FIG. 4.

Since the swabbing pad 54 is now covered by the second portion 40 in a light-tight environment, ambient light is no longer incident upon the swabbing pad 54.

Figure 5A:
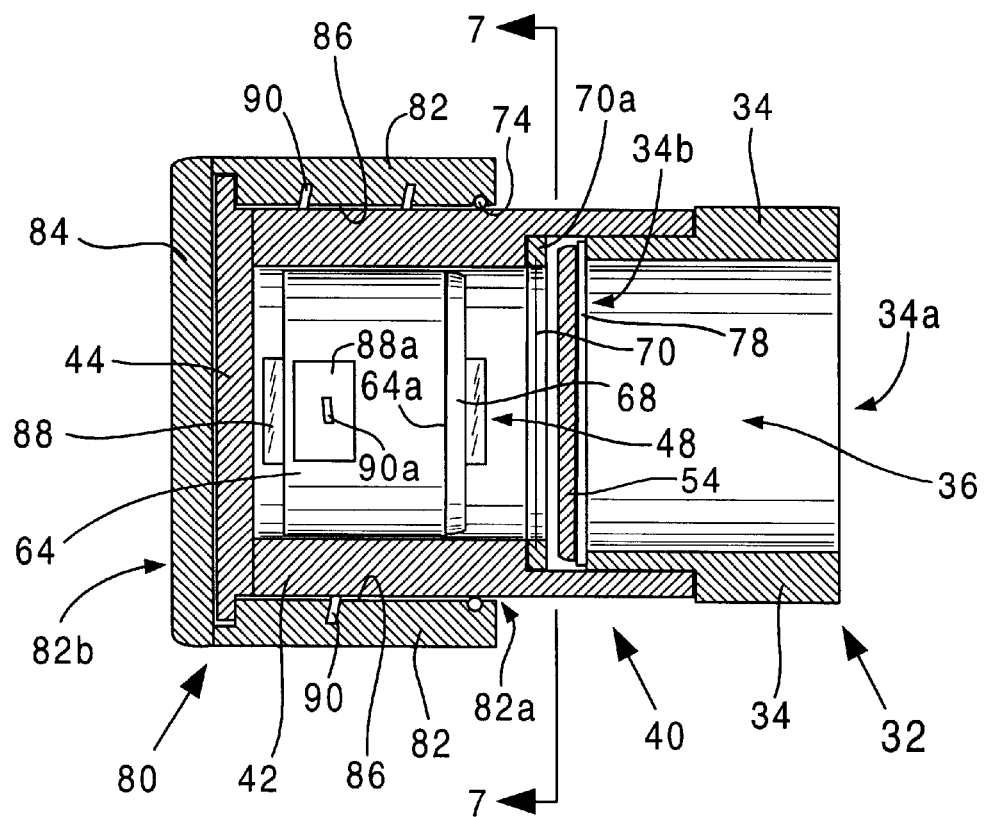
Figure 6A:
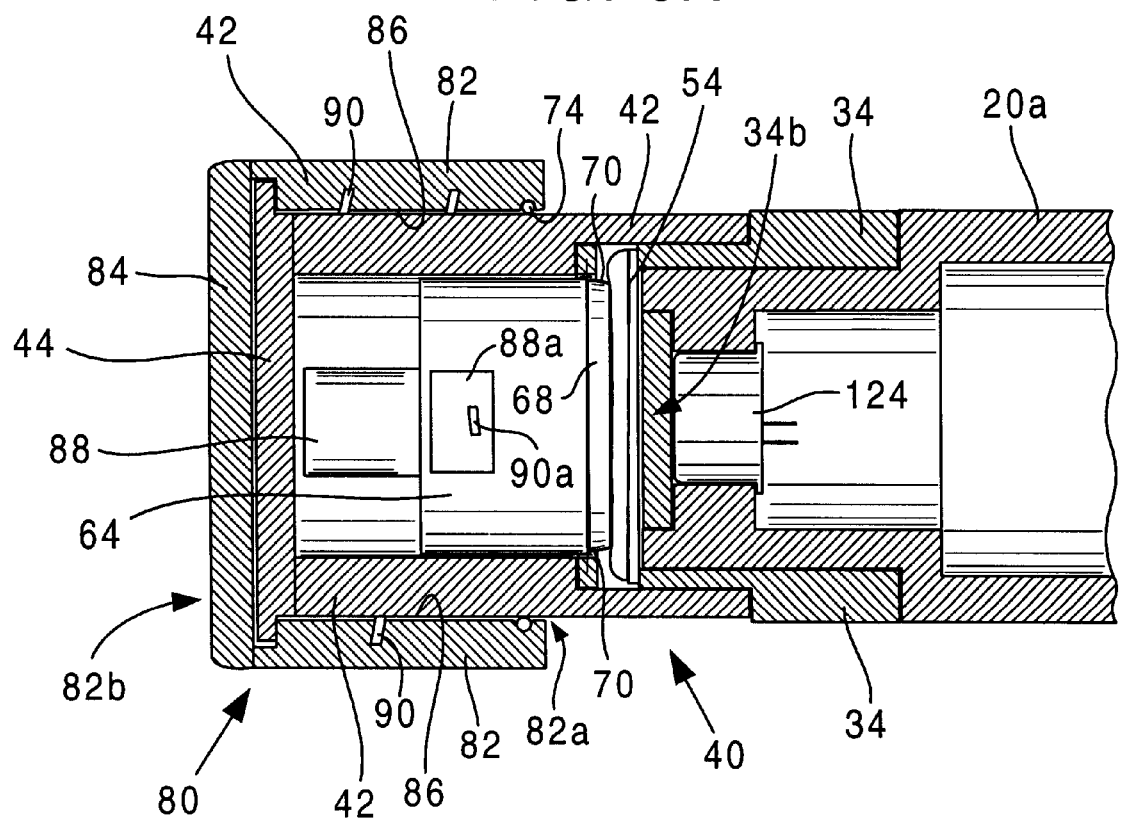
FIGS. 6A and 6B show the detector cap assembly of FIGS. 5A through 5C after being installed: over an embodiment of the photodiode detector head assembly and actuated to commence assaying activities.

As can be seen in FIGS. 5A and 6A, the second portion 40 of the detector cap assembly 30 is preferably structured having a wall structure 42 and a top surface 44. The wall structure 42 and the top surface 44 establish an internal chamber 48 and an opening 52 (as shown in FIG. 5C). The opening 52 shown in FIG. 5C is configured to enable the second portion 40 to be removably installed onto the first portion 32, so as to cover the swabbing pad 54 in order to cap the first portion 32 in the light-tight manner. Therefore, the second portion 40 is installed onto and over the first portion 32 so as to substantially limit or prevent ambient light from being incident upon the swabbing pad 54. This need to cover or cap the swabbing pad 54 is essential to eliminate ambient light from being incident upon the swabbing pad 54 and the photo detection means of the detector head assembly 12 while the low level luminescent emissions of an assaying reaction are being detected and measured.

As shown in FIGS. 5A through 6B, the second portion 40 is configured to house a movable structure 64 within the chamber 48. The movable structure 64 of the embodiment may be embodied having a substantially flat surface 64a, as illustrated, that is oriented proximate and parallel to the plane of the opening 52 of the second portion 40. The movable structure 64 is also configured to be movable between a first retracted position away from the opening 52 (as illustrated in FIG. 5A) and a second deployed position (as illustrated in FIG. 6A), which is more proximate to the opening 52. A porous pad 68 is fixed to and arranged to substantially cover the flat surface 64a of the movable structure 64. In the embodiments of the detector cap assembly 30 shown in FIGS. 5A through 6B, the porous pad 68 may be impregnated with suitable dried reagents that are activated by wetting when brought into pressure contact with the wetted swabbing pad 54 (as depicted in FIG. 6A). It should be noted that the term 'pressure contact' may be assumed to indicate that the porous pad 68 is brought into contact with the swabbing pad 54 with a sufficient pressure to enable the wetness of the swabbing pad 54 to wet and activate the dried reagents that impregnate the porous pad 68. Skilled individuals will understand that the reagents will then dissolve and be drawn from the porous pad 68 to the swabbing pad 54 in a most preferred embodiment of the invention, when the analyte has been collected upon the swabbing pad 54 and sufficient luciferase-luciferin dried reagents are employed to produce a luciferase-luciferin reaction, low level luminescent emissions will be produced. It may be noted that the expression "possibly resulting in one of either a bioluminescent and a chemiluminescent assaying:reaction producing low level luminescent emissions" is intended to indicate that an assaying reaction will occur at a sufficient intensity, if an analyte (e.g., microbial matter) is present in a sufficient volume on the swabbing pad 54. Conversely, if a sufficient volume of analyte is not present, an assaying reaction will not provide emissions with a sufficient intensity to be detected and properly measured.

Figure 5B:
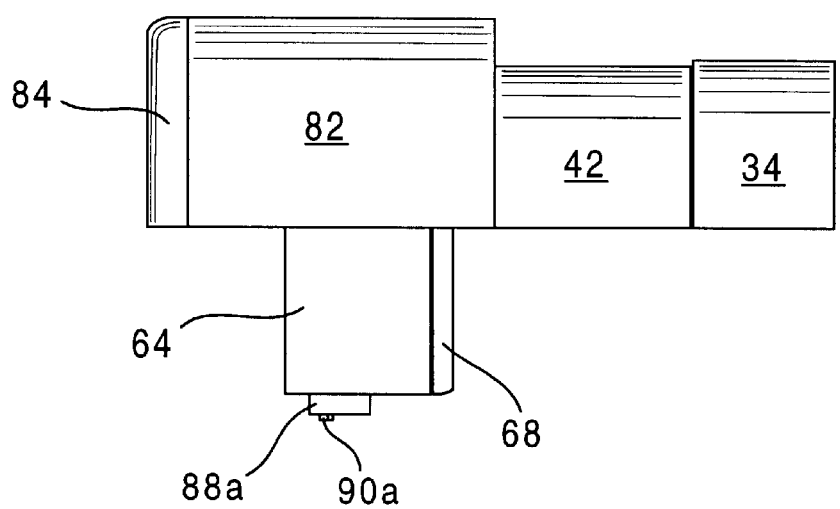

In accordance with the present invention, a preferred method of swabbing a test surface in order to collect and indicate the presence of an analyte will now be discussed. It must be noted that the methods of the invention may be realized with the exemplary structures and arrangements provided herein, as well as other structures providable by skilled individuals after carefully reviewing the content of the present disclosure. The method may involve several preliminary steps, such as installing the detector cap assembly 30 upon the detector head assembly, calibrating the luminometer 10, and other possible initial steps. Next, as shown in FIG. 3, the swabbing pad 54 is exposed. A user may then swab a selected test surface(s) by contacting the first surface 54a of the pre-wetted swabbing pad 54. As discussed, swabbing pad 54 may be structured with the first surface 54a shaped and configured for contacting the test surface to collect therefrom available analyte. As such, the first surface 54a may be substantially flattened, as can be seen in FIGS. 3, 5A and 5b, or alternately, the first surface 54a may assume other shapes including conical, wedge, or a traditional 'swab' shape. The actual shape of the first surface 54a may be best determined by the shape and texture of the test surface to be swabbed. Once one or more test surfaces have been swabbed to enable analyte to be collected upon the swabbing pad 54, the second portion 40 of the detector cap Assembly 30 may be re-installed over the swabbing pad, as shown in FIG. 4, establishing the light-tight environment. Next, the first surface 54a of the swabbing pad 54 is brought into pressure contact with suitable dried reagents. For example, a porous pad 68 that is impregnated with suitable dried reagents may be moved and brought into pressure contact with the swabbing pad 54. As indicated, this causes the wetting of the dried reagents within or upon the porous pad 68, causing the reagents to dissolve and be drawn from the porous pad 68 to the swabbing pad 54. If suitable quantities of analyte have been collected from the test surface, a detectable low level luminescent assaying reaction may be efficiently detected and quantified.

In preferred embodiments of the invention, when the swabbing pad 54 is brought into pressure contact with a suitably shaped porous pad 68, the first surface 54a and the second surface 54b of the swabbing pad are compressed with the distance between at least one portion of the first surface 54a and the second surface 54b being substantially reduced with said pressure contacting. This will clearly result in a better wetting of the porous pad 68. In addition, such a compression of the swabbing pad 54 will importantly provide for a more efficient detecting of any emitted low level luminescent emissions, with the detecting realized by a detection means that is efficiently (e.g., closely) positioned proximate to the second surface of the swabbing pad. It may be noted that the term 'sufficiently reduced', as applied above to the compression of the swabbing pad, may be assumed to indicate that the distance between at least apportion of the first surface 54a and the second surface 54b of the swabbing pad is reduced by at least 15% to 50% (or more) of the uncompressed distance therebetween.

An important characteristic of preferred embodiments of the present invention is the use of a swabbing structure wherein swabbing and collecting of analyte occurs on a first side or surface (e.g., first surface 54a of swabbing pad 54), with low level luminescent emissions emitted from a second side or surface (e.g., second surface 54b) being coupled to, or received by, a suitable photodiode detecting means and 'efficiently detected' thereby. As can be seen in FIG. 6A, the pressure contacting of the swabbing pad 54 and the porous pad 68 occurs within close proximity of the photodiode 124—providing for a very efficient detection arrangement.

Figure 10B:
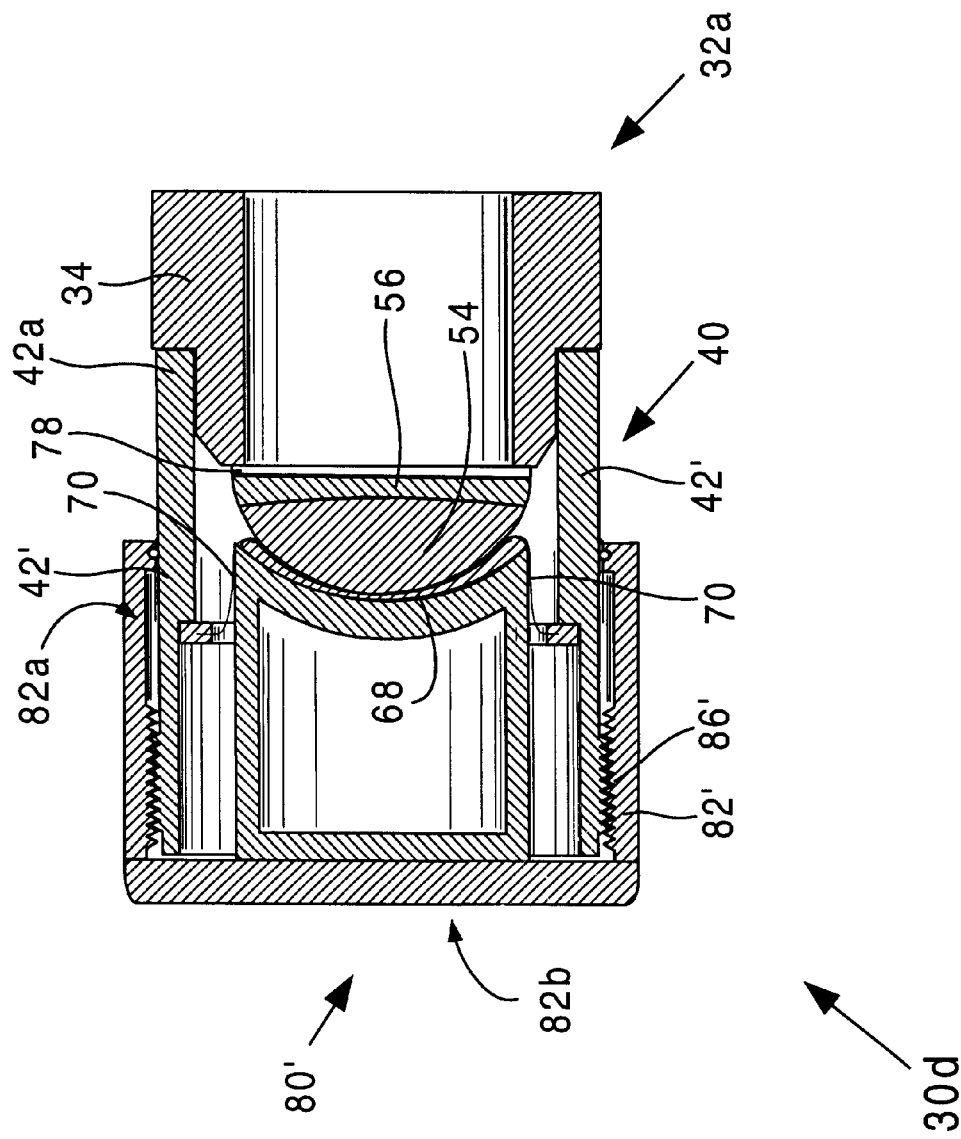
Figure 11A:
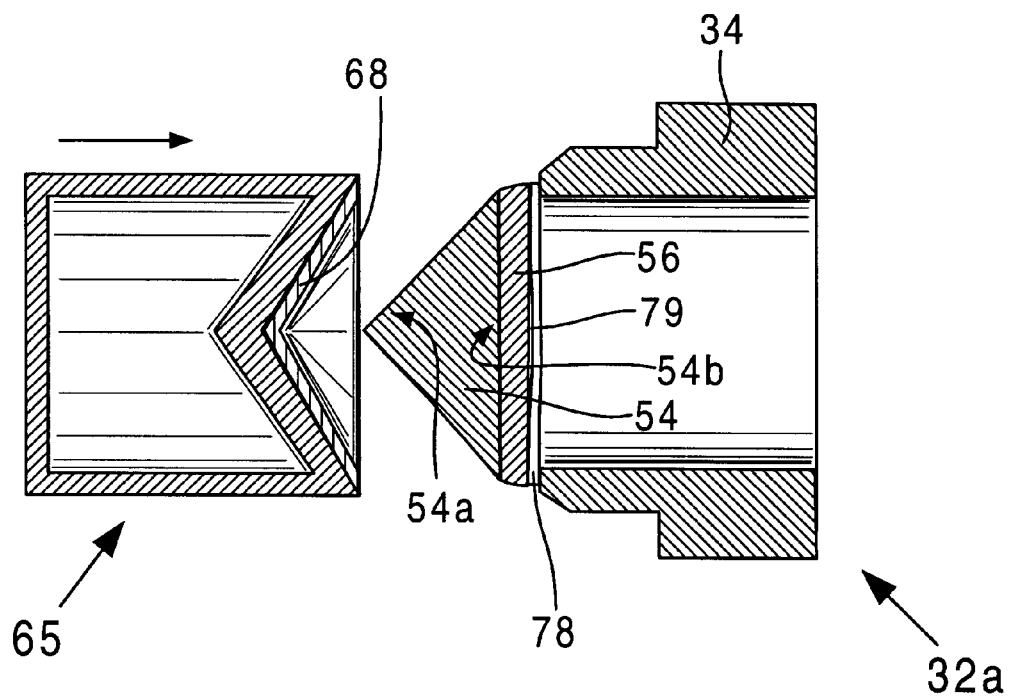
FIGS. 11A and 11B illustrate sectional views of other preferred embodiments of swabbing structures, specifically providing examples of swabbing pads having differing shapes.
Figure 11B:
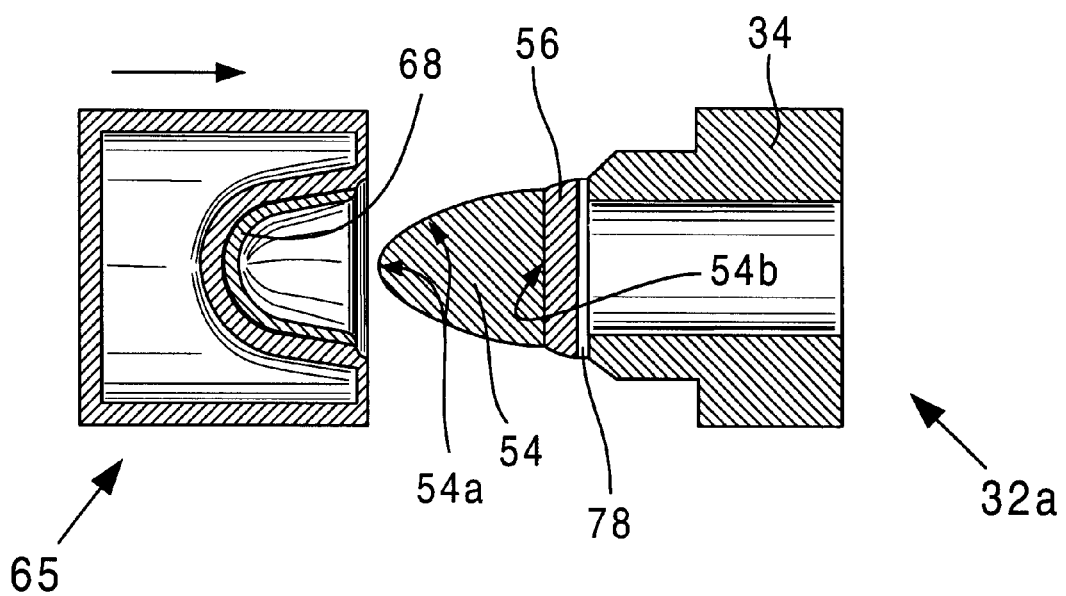

It is important to note that items such as the swabbing pad 54 and the porous pad 68, as well as other structures to be discussed when referring to FIGS. 10 through 11B, are preferably formed of a material having bright, reflective color, and a porosity or "openness" of 60% to 95%. Accordingly, porous polymer pads and more generally porous polymeric materials, would provide an example of a most preferred material having a bright reflective coloring and a sufficient openness suitable for use with the swabbing structures of the invention. The use of bright and open materials is helpful for several reasons. First, the openness enables the pre-wetted swabbing pad 54 absorb and retain a sufficient volume of wetting agent for both swabbing and pressure contacting purposes. In addition, an assaying reacting producing low level luminescent emissions may be easily supported thereupon. A most interesting consequence of the use of a swabbing structure of the present invention is that any assaying reaction produced upon the swabbing pad 54, the porous pad 68, or other included (porous) items, results in luminescent emissions being reflected and 'channeled' or transmitted to other portions or areas of the included porous pads. As such, it may be said that the reflective coloring and open/porous structure of these items 'enhances' the ability to detect and quantify the luminescent emissions produced by a reaction occurring thereupon.

It may be assumed that emitted photons comprising the luminescent emission, which are produced by the assaying reaction, may reach the photodiode 124 or an equivalent means by at least one or more of the following mechanisms: (1) directly from the swabbing pad, or another pad superposed over the window 14, (2) indirectly via reflected luminescent emissions (say produced on or near the porous pad 68), and (3) emissions produced by a liquid phase or layer. Each type of emission delivery mechanism will be briefly discussed while referring to the structures of FIGS. 5A to 6B. It should be noted that the definitions and descriptions of these terms may be extended and applied to other, possibly quite different structures. Direct emissions are emissions associated with a portion of an assaying reaction that is occurring quite close to, if not upon, the second surface 54b of the swabbing pad 54. Indirect (reflected) emissions are emissions that are produced in more distant portions of the assaying reaction (say a portion of the reaction occurring near or on the porous pad 68) that are reflected and transmitted via the openness of the employed pads of the swabbing structure. A term that may be used to describe the inherent mechanism (of the employed porous pads) to deliver indirect emissions is 'reflective porosity'. Finally, liquid phase emissions are emissions that may occur (or caused to occur) in a layer of liquid situated between the second surface 54b of the swabbing pad 54 and the second barrier 78. This liquid may be composed of, or include, wetting agent, analyte, and reagents from the porous pad 68.

Importantly, it is the above emission delivery mechanisms, and equivalents, in combination with the swabbing structures of the present invention, that provide the unexpected result of being able to accurately detect and quantify the low level luminescent emissions of the assaying reaction using means based on inexpensive photodiode semiconductor detectors (as opposed to more sensitive and costly PMT based luminometer devices).

Figure 6B:
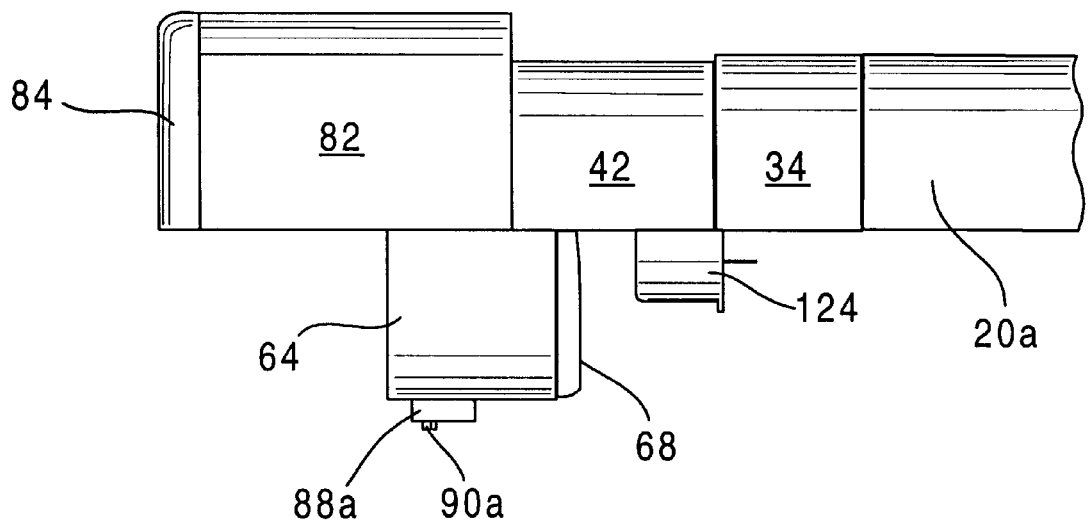

Returning to FIG. 5A, skilled individuals will appreciate the need to prevent moisture and humidity from prematurely activating the dried reagents of the porous pad 68. If the detector cap assembly (including the porous pad 68) is packaged in a suitable packaging arrangement, then moisture and humidity may be blocked by such a packaging. Alternately, a means may be provided to frangibly seal the internal chamber 48 until such time that the movable structure 64 is to be moved from the first retracted position to the second deployed position. Also, the means must be arranged to enable the suitable wetting of the porous pad 68 when the pressure contacting of the swabbing pad 54 and porous pad 68 occurs. Such a sealing or barrier means may be provided by a first barrier 70, which is structured to be thin and frangible. The first barrier 70 is arranged to cover the opening 52 of the second portion 40 in a recessed fashion, as illustrated is FIGS. 5A and 6A. A support ring 70a may be provided to support the frangible barrier 70, as illustrated. The arranging of the first barrier 70 in the recessed fashion enables a portion of the internal chamber 48 having the porous pad 68 and the movable structure 64 contained therein to be hermetically sealed while the movable structure 64 is in the first retracted position. Thus, the hermetically sealed portion of the internal chamber 48 enables the porous pad 68 to remain dry (while the movable structure 64 is maintained in the first retracted position). The recessed fashion of positioning the first barrier 70 will also enable the photodiode detector head assembly (and the first portion 32) to be placed into the second portion without rupturing the first or frangible barrier. Accordingly, after swabbing has been completed, possibly causing analyte to be collected upon the swabbing pad 54, the second portion 40 may be re-installed over the first portion 32. The movable structure 64, including the porous pad 68, may next be moved from the first retracted position (FIG. 5A) to the second deployed position, as is shown in FIGS. 6A and 6B, causing the first barrier 70 to be ruptured.

Figure 7:
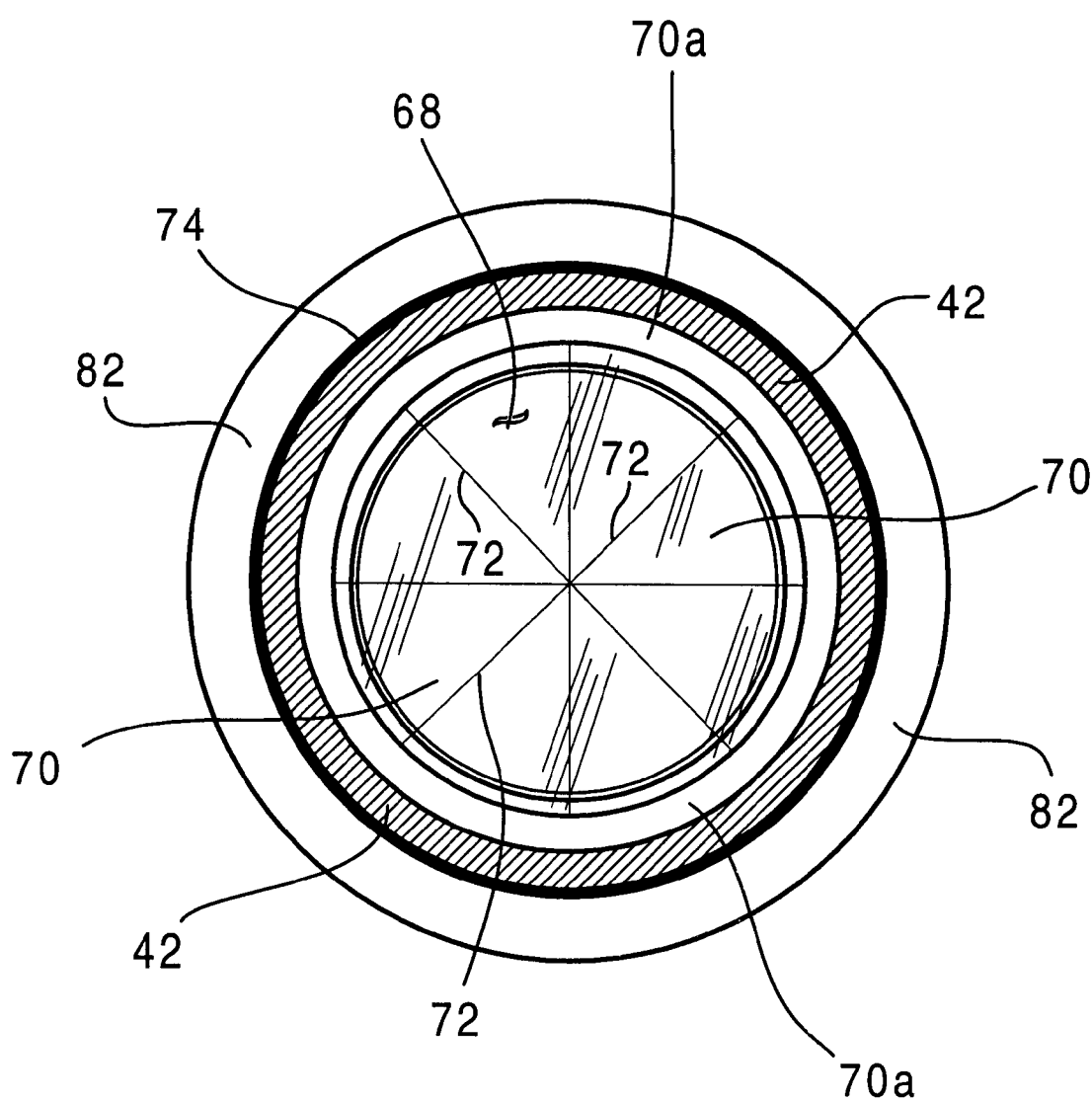
FIG. 7 illustrates a partially sectioned plan view of a portion of the detector cap assembly taken along a line 7—7 of FIG. 5A.

It should be noted that the first barrier 70 must be structured to be appropriately ruptured when the movable structure 64 is moved from the first retracted position to the second deployed position. The term 'appropriately rupturing' (and equivalents) are to be defined as rupturing in a suitable fashion so as to enable sufficient wetting agents of the swabbing pad 54 to wet the dried reagents of the porous pad 68 and cause a desired assaying reaction (when sufficient analyte is present). As shown in FIG. 7, the first barrier 70 may be scored with score lines 72 that are provided to establish rupture or tear locations to facilitate the appropriate rupturing of the first barrier 70. Further, if the first barrier 70 is provided by a stretched, possibly elastic material, the rupturing may result in a maximal direct contacting of the swabbing pad 54 and the porous pad 68 when the pressure contacting is established. Therefore, when the movable structure 64 is moved from the first retracted position to the second deployed position, the first barrier 70 is ruptured, the porous pad 68 is brought into pressure contact with the swabbing pad 54 causing the dried reagents to be dissolved, and drawn to and activated by the wetness of the pre-wetted swabbing pad 54. If an analyte is present on or in the swabbing pad, the activation of the dried reagents will result in at least one of a bioluminescent assaying reaction and a chemiluminescent assaying reaction producing the low level luminescent emissions that are detectable by the photodiode detector head assembly 12 of the luminometer 10.

It is important to understand that in order to establish the light-tight environment, and restrict ambient light from being incident upon the swabbing pad 54, the wall structures of the first and second portions, as well as portions of the housing of the luminometer 10, must be suitably structured of opaque materials. Further, although said wall structures are preferably cylindrical in shape, other suitable and possibly preferable shapes and mechanical arrangements may be provided by skilled persons. As such, even though the photodiode detector head assembly 12 is illustrated as being cylindrical and shown to protrude from the housing 20 so that the detector cap assembly 30 may be snugly fit over the housing portion 20a (fixed there in the light-tight manner), many other arrangements are possible and contemplated. For example, the window 14 may be situated within a housing configuration providing a female bayonet mounting arrangement around the window. When considering this configuration, the detector cap assembly 30 may be arranged with a male bayonet structure which is arranged to mate to and engage a female bayonet structure, causing the removable fixing to the photodiode detector head assembly 12 of the housing 20, as required. Therefore, even though the illustrated embodiments of the present invention are depicted employing tapered and friction based engaging arrangements, other structures including bayonet structures and simple treading arrangements may be alternately employed.

Figure 8A:
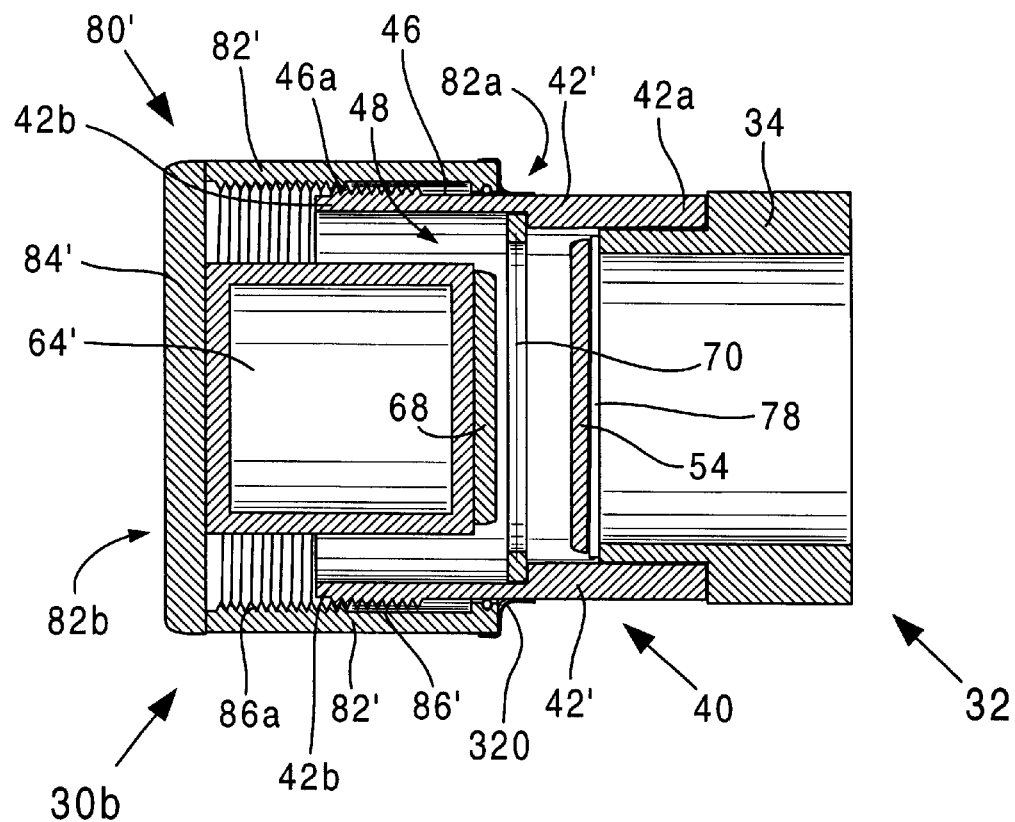
FIGS. 8A and 8B provide sectional side views of another embodiment of the detector cap assembly in accordance with the invention.

As illustrated in FIGS. 5A, 6A, and 8A, a transparent supporting and fluid impervious second barrier 78 may be provided under the swabbing pad 54 and over the second opening 34b of the first portion 32. The second barrier 78 may be included to seal the second opening 34b to prevent the transport of moisture therethrough. There are at least two situations where such a transport may occur. First, when the detector cap assembly 30 is not installed over the detector head housing 20a (i.e., over the photodiode detector head assembly 12), moisture may pass through the first opening 34a of the first portion 32 and possibly contaminate the swabbing pad 54. Alternately, when the movable structure 64 is moved to the deployed position (as shown in FIG. 6A), it is desirable to prevent the transport and loss of any of the wetting agent through the second opening 34b of the first portion 32. Therefore, when the second barrier 78 is omitted, the transport and loss of wetting agent may be controlled by the window 14 of the detector head assembly 12. However, as skilled persons would appreciate, the inclusion of the second barrier 78 prevents any contaminants, analyte, and or other microbial matter from passing from the swabbing pad 54 to the photodiode detector head assembly 12 or visa-versa.

A primary purpose for employing a (volume of a) wetting agent is to enable analyte to be easily collected, while also providing a means to wet the dried reagents of the porous pad 68. As skilled persons would appreciate, when considering appropriate wetting agents to employ, a volume of sterile water, a nucleotide releasing reagent, and or a variety of well known buffering agents may be used. The particular wetting agent may actually be determined as a function of the particular analyte to be detected or assayed, as well as the particular dried reagents employed to impregnate the porous pad 68. In addition, when considering preferred material suitable for providing the swabbing pad 54, known substances such as a cotton or a polymer pad may be selected. However, it should be noted that any substance which enables a sufficient volume of the wetting agent (say for example 0.1 to 1 ml) to be absorbed, and further enable the analyte to be collected during swabbing activities, may be employed. Similarly, when considering materials that may be employed to provide the porous pad 68 a number of known materials will suffice. However, a preferred material contemplated to embody the porous pad 68 include one or more layers of a (possibly paper) blotter material, a thin sponge-like material, and or one or more layer of a porous polymer sheet material.

Figure 8B:
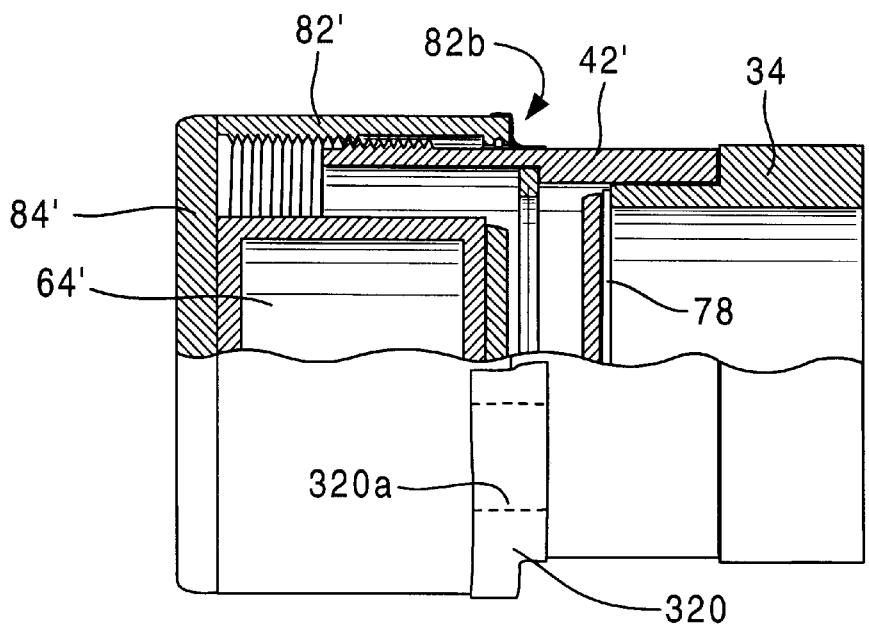

Returning to FIGS. 5A and 6A, one preferred embodiment of the present invention is structured with the second portion 40 that is comprising an outer cap-like portion 80, preferably having a cylindrical wall structure 82 (or a suitable wall structure that matches the shape of the second portion 40 of the detector cap assembly 30). An interior surface 86 of the wall structure 82 of the cap-like portion 80 may include a spiral groove 90 cut or formed therein. As can be seen, the cap-like portion 80 is coextensively and co-axially disposed over a second portion 40 and structured to be rotatably fixed thereto so as to rotate around a center (or a longitudinal) axis common to each of the outer cap-like portion 80 and the second portion 40. The wall structure 42 of the second portion 40 is configured having at least one slot 88 formed therein. The slot 88 may be arranged to form an essentially rectangular elongated opening, that is oriented parallel to, or along, the center axis of the second portion. The movable structure 64 of the detector cap assembly 30 of FIGS. 5A through 6B may be preferably structured with a cylindrical shape having at least one raised block 88a that is sized to fit into and slide somewhat freely up and down the slot 88. An angled follower tab 90a extending radially from the raised block 88a extends through the slot 88 and is arranged to mate !to and follow the spiral groove 90 of the cap-like portion 80. Accordingly, the movable structure 64 is configured to be movable from the first retracted position, as clearly seen in FIG. 5A, to the second deployed position, as clearly seen in FIG. 6A, by rotating the outer cap-like portion 80 with respect to the second portion 40. That is, as the outer cap-like portion 80 is rotated with respect to the second portion 40, the follower tab 90a causes the movable structure 64 to be moved from the first retracted position (away from opening 52 of the internal chamber 48 of the second portion 40) to the second deployed position (more proximate to the opening 52). This kind of structure, and equivalents thereof, that enable the movable structure 64 to be moved up and down the slot 88, may be provided by skilled individuals, in many forms. As shown in FIGS. 5A and 8A, an o-ring (or equivalent structures) may be included to maintain a hermetic seal of the portion of the interior chamber that houses the movable structure 64. A safety locking means 320 (and equivalent functional structures), as depicted in FIGS. 8A and 8B, may be included to prevent the cap-like portion 80 or 80' from inadvertently rotating (with respect to the second portion 30). The safety locking means (e.g., a securing band) may include perforations 320a to enable a user to easily and quickly remove the safety locking means 320. Skilled persons will recognize that other structures may be provided to realize the functional characteristics of the safety locking means 320.

Importantly, it must be noted that any suitable structure that enables a user to move the movable structure 64 from the first retracted position to the second deployed position, with a light-tight environment, is contemplated as being within the scope of the present invention. For example, another embodiment of the detector cap assembly (30b) is illustrated in FIGS. 8A and 8B. The detector cap assembly 30b is arranged with an alternate structure to suitably move the movable structure 64 from the first retracted position to the second deployed position. As can be seen, the second portion 40' is comprised of an outer cap-like portion 80' having a preferably cylindrical wall structure 82' that is closed by a top surface 84' at a second (closed) end 82b. The first end 82a of the wall structure 82' of the cap-like portion 80' is open. The wall structure 82' is arranged with a threaded portion 86a that is provided on an interior surface 86' thereof. As shown in FIGS. 8A and 8B, the threaded portion 86a of the interior surface 86' would preferably begin proximate to the second (closed) end 82b and extend a suitable distance (e.g., approximately halfway) down the height of the cap-like portion 80' along the interior surface 86'. The second portion 40' of the embodiment of FIGS. 8A and 8B is arranged (much like the second portion 40 of previously discussed embodiments) having its wall structure 42', and a first end 42a and a second end 42b. An outer surface 46' of the wall structure 42' of the second portion 40' is configured with a treaded portion 46a that is structured to mate to and engage the threaded portion 86a of the interior surface 86' of the outer cap-like portion 80'. The respective engaged threaded portions thereby enabling the outer cap-like portion 80' to move along a common center or longitudinal axis of each of the second portion 40' and the outer cap-like portion 80' when the outer cap-like portion 80' is rotated around said center axis with respect to the second portion 40'. This rotation effectively causes the outer cap-like portion 80' to be screwed coaxially and (at least partially) coextensively down and over the second portion 40'.

As is shown in FIGS. 8A and 8B, the top surface 84' of the outer cap-like portion 80' is structured with a movable structure 64' fixed to the top surface 84' and extending down into the second portion 40'. As such, and much like the movable structure 64 of the embodiment of FIGS. 5A through 6B, the movable structure 64' is movable from a first retracted position to a second deployed position when the outer cap-like portion 80' is rotated, and coaxially and coextensively screwed down over the second portion 40'. As discussed above, the movement of the movable structure 64' to the second deployed position will cause the frangible first barrier 70 to be ruptured, and effect the placement of the porous pad 68 in pressure contact with the swabbing pad 54.

Figure 9A:
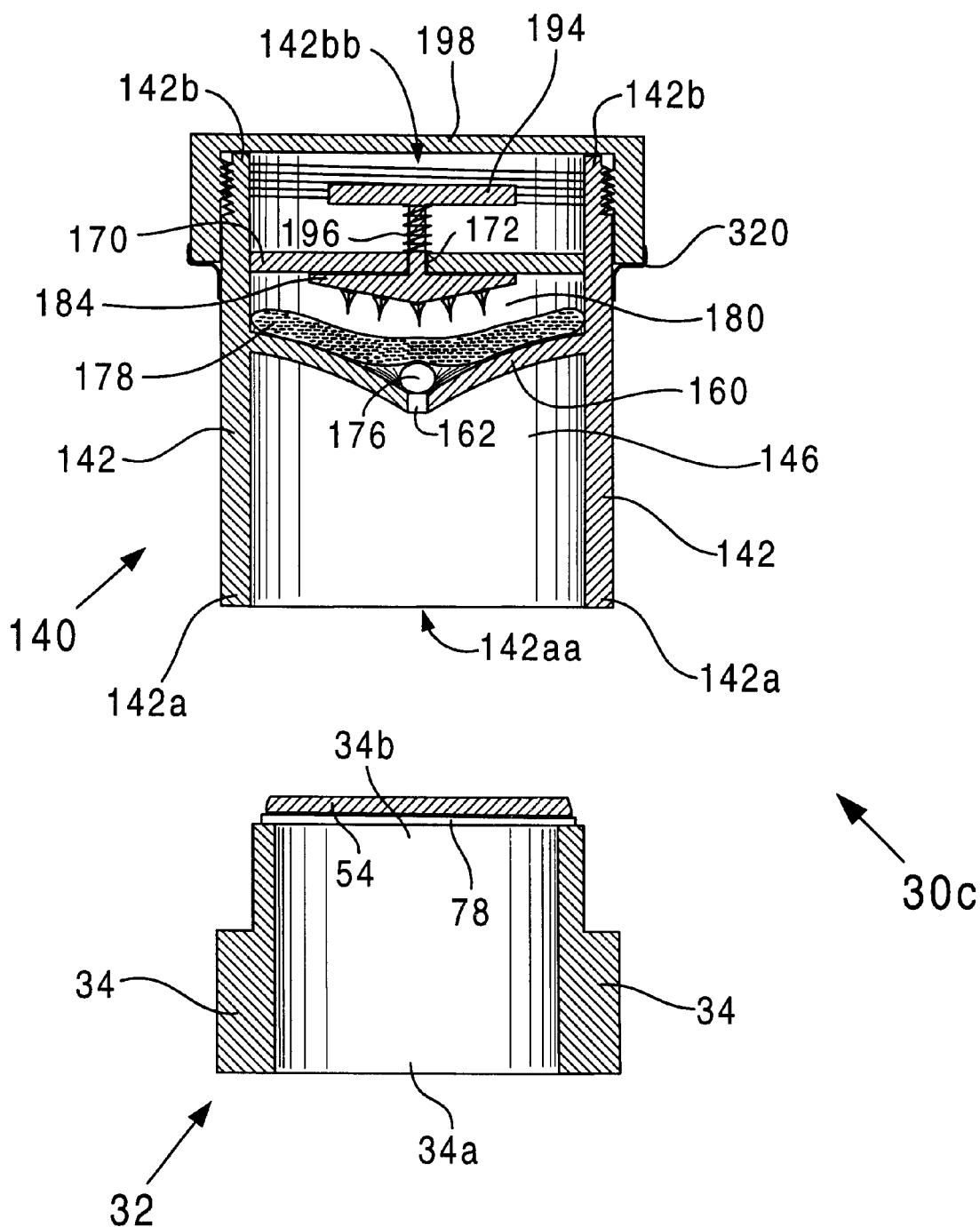
FIG. 9A illustrates yet another embodiment of the detector cap assembly shown in a sectional side view.

Turning now to FIG. 9A, there is illustrated yet another embodiment of a detector cap assembly 30c depicted in a cross sectional view. The first portion 32 is equivalent to the first portion as shown and described in FIGS. 2 through 8B. A second portion 140 is structured having a vertical wall structure 142 and a top end 142b and a bottom end 142a. The second portion 140 is configured with a top opening 142bb at the top end 142b and a bottom opening 142aa at the bottom end 142a. The bottom opening 142a is, as discussed above, arranged to enable the second portion 140 to be removably installed onto the first portion 32 to cap the first portion and the swabbing pad 54 in the light-tight manner.

The second portion 140 further includes a first partition wall 160 oriented substantially traverse to and preferably parallel with the bottom opening 142aa, and within the wall structure 142 of the second portion 140. The first partition wall 160 is suitably spaced from the bottom end 142a so as to form a cavity 146. The first partition wall may be configured as depicted with a substantially concaved shape. A portion of the cavity 146 proximate to the bottom opening 142aa is filled by the first portion 32 when installed on the second portion 140. The first partition wall 160 further is provided with at least one hole 162. A second partition wall 170, which is preferably oriented substantially traverse to the t op opening 142bb, and within the wall structure 142 of the second portion 140 so as to form a chamber 180 that is situated above the cavity 146. The second partition wall 170 is arranged with a hole 172. The function provided by the hole 172, or an equivalent arrangement will be discussed below. A sealed fluid holding envelope 178 is provided and situated in the chamber 180 to hold a volume of a suitable wetting agent. Also contained in the chamber 180 is at least one pellet 176 of dried reagent that is situated between the fluid holding envelope 178 and a top surface of the first partition wall 160. The pellets 176 are to be sized having a diameter greater than each hole 162 provided in the first partition wall 160 so that the pellets 176 not are easily moved through the respective holes 162 until they are at least partially dissolved by the wetting agents contained in the fluid holding envelope 178.

In order to activate the pellets 176 the fluid holding envelope 178 must be ruptured or perforated to release the (volume of) wetting agent contained therein. Accordingly, some perforation means, which is activated by a user, must be provided. For convenience the perforation means may be structured to be activated from a location proximate to the top opening 142bb, for example, above the second partition wall 170. It would also be desirable for said perforation means to be substantially housed within the chamber 180 and arranged to easily be actuated to perforate the fluid holding envelope 178 in order to release the volume of wetting agent into the chamber 180 to activate and dissolve the pellets 176. An embodiment of the perforation means, which is illustrated in FIGS. 9A, 9B and 9C, includes a perforation disk 184 located in the chamber 180 above the fluid holding envelope 178. The perforation disk 184 is structured with a first surface 184a and a second surface 184b (as best seen in FIGS. 9B and 9C). The first surface 184a is arranged with a plurality of piercing points 186 extending (downwardly) from the first surface and toward the fluid holding envelope 178. Preferably the first surface 184a is oriented substantially parallel to and spaced from the fluid holding envelope 178 when the perforation means is not actuated (as shown in FIG. 9B). A shaft 190 is included having a first end 190a and a second end 190b. The first end 190a is fixed to the second surface 186b of the perforation disk 190 so that the shaft 190 passes through the hole 172 in the second partition wall 170 with the second end 190b of the shaft 190 situated at the location proximate to the second opening 142bb, and above the second partition wall 170. Accordingly, the second end 190b of the shaft 190 may be employed to actuate the perforation disk 184, as depicted in FIG. 9C, to perforate the fluid holding envelope 178. In a preferred embodiment of the detector cap assembly 30c, a button 194 may be fixed to the second end 190b of the shaft 190 to assist in activating the perforation means. When the button 194 is used to depress the shaft 190, the perforation disk 184 is moved from a first position (as shown in FIG. 9B) to a second position (as shown in FIG. 9C). In the first position the perforation disk 184 is spaced from the fluid holding envelope 178 and the volume of wetting agent is sealed therein. It may be noted that the perforation disk 184 may be biased in the first position by the inclusion of a spring 196, which is shown in FIGS. 9A. When the second end 190b of the shaft 196 is depressed to move the perforation disk 184 to the second position, the fluid holding envelope 178 is perforated releasing the wetting agent. The released wetting agent would then cause the pellet 176 of dried reagents to dissolve. The wetting agents and reagents may then pass through the hole 162, and contact and wet the swabbing pad 54.

Therefore, the actuation of the perforation means causes the release of a volume of the wetting agent. The released wetting agent results in the wetting and at least partially dissolving the one or more pellets 176 provided to cause the formally dried reagent provided thereby to be carried thorough the hole 162 in the first partition wall 160 to wet the swabbing pad 54. The wetting of the swabbing pad, as discussed above, may result in an assaying reaction producing the low level luminescent emissions that are detectable by the photodiode detector head assembly (if a suitable volume of analyte is present on the swabbing pad 54). It should be noted that in order to prevent the accidental actuation of the perforation means (e.g., the perforation disk 184), a lid 198 may be provided. As depicted in FIG. 9A, to actuate the perforation means, the lid 198 would be screwed off, exposing the button 194 (or an equivalent actuation structure).

As with the embodiments of FIGS. 5A and 8A, the second barrier 78, which may simply be termed 'a transparent fluid impervious barrier', may be included with detector cap assembly 30c. Although, the second barrier 78 prevents wetting agent from passing through the second opening 34b of the first portion 32, another function may be provided by the inclusion of the second barrier 78. This additional function is to prevent moisture and humidity from entering the cavity 146 by passing through the swabbing pad 54. Any moisture and humidity that enters the cavity 146 will ultimately pass through the hole 162. This should be avoided in order to keep each pellet 176 (and the reagent contained therein) completely dry and stable.

Alternate swabbing structures are further contemplated for use with the above disclosed methods and means to collect, detect, and quantify analyte in accordance with the present invention. For example, as can be seen in FIGS. 10A and 10B, a modified embodiment of a detector cap assembly 30 may be structured with a possibly preferred first portion 32a. The first portion 32a includes a preferably substantially flattened support and reading pad 56 having a first surface 56a (or first side) fixed to the second surface 54b of the swabbing pad 54. The support and reading pad 56 would most preferably be provided by a material having a bright, reflective coloring, and a high porosity or openness of 60% to 95%. The first surface 56a of the support and reading pad 56 may be said to be superposed by the second surface 54b of the swabbing pad 54, as shown in FIG. 10A. As discussed, the first portion 32/32a may be structured with a wall portion 34 and a second (transparent) barrier 78, which may be considered a means to support the support and reading pad 56, and therefore the swabbing pad 54. The structure of FIG. 10A is specifically contemplated to enable the swabbing of a test surface and subsequently facilitate the detecting, in a light-tight environment, of any low level luminescent emissions emitted, at minimum, from a second side 56b of support and reading pad 56. This is similar to the function of the previous embodiments, with the exception that the direct detecting of luminescent emissions (of previous embodiments) is made from the second surface 54b of the swabbing pad 54, instead of the second surface 56b of the support and reading pad 56.

The inclusion of the support and reading pad 56, as depicted in FIG. 10A, provides several functional improvements. First, the support and reading pad 56 may be formed of a material having a higher openness, yet being embodied to be stiffer (or firmer) than the material utilized to provide the swabbing pad 54. As such, when the pressure contacting of the porous pad 68 occurs, as shown in FIG. 10B, at least a portion of the wetting agent solution (including reagents and analyte) is absorbed by and moved into the support and reading pad 56. Therefore, the swabbing structure of FIGS. 10A and 10B may provide for an improved ability to detect and quantify the luminescent emissions of the assaying reaction, primarily due to an increased portion of the assaying reaction occurring in the very porous and reflectively colored support and reading pad 56. The support and reading pad 56 may be said to have a high 'reflective porosity', preferably greater than of equal to the swabbing pad 54 and the porous pad 68.

It must be noted that other preferred embodiments of a swabbing structure of the present invention are certainly providable. For example, consider an embodiment that omits the porous pad 68 and provides for a modified support and reading pad (not illustrated). The modified support and reading pad, which may be termed a reagent impregnated reading structure, is impregnated with the dried reagents provided in above embodiments within the porous pad 68. As such, the modified support and reading pad, now essentially provides for or includes the functions of the porous pad 68 and the support and reading pad 56. A movable structure, such as a modified movable structure 64 (not illustrated) is included having a plurality of piercing points, or functionally equivalent structures. This modified structure is an example of an arrangement that provides for compression and piercing when activated. That is, the piercing points (or equivalents thereof) are provided to compress a swabbing pad 54 and at the same time puncture and form openings in a suitably provided moisture barrier. Such a moisture barrier is included to prevent moisture and humidity from compromising the reagents impregnated into the modified support and reading pad. Preferred materials to be used to provide this moisture barrier would be a thin foil or most preferably a thin and frangible transparent membrane, say formed of a stretched, thin plastic sheathing.

An embodiment of a preferred method for use with the swabbing structure discussed in the preceding paragraph, would be similar to the methods discussed above. For example, after swabbing of the test surface is completed, a suitable structure would be used to position the modified movable structure—within a light-tight environment. Next, the modified movable structure is brought into pressure contact with a swabbing pad such as the swabbing pad 54. The plurality of piercing points would then compress the swabbing pad and eventually piece the above described moisture barrier. Wetting agents used to pre-wet the swabbing pad 54 would be forced and or drawn into the modified support and reading pad, possibly causing an assaying reaction that produces the low level luminescent emissions. As with other embodiments, a photo detection means (such as photodiode 124) would be positioned proximate to a second barrier, such as the second barrier 78 of FIGS. 11A or 11B. It may be noted that the moisture or hermetic sealing of the modified support and reading pad may be provided by the combination of the moisture barriers (not illustrated).

Another important feature and modification of the present invention is shown, in an exemplary fashion, in FIG. 11A. The embodiment of a portion of the first portion 32a includes a second barrier 78 forming a small pocket 79 between a second surface of the support and reading pad 56 and the second barrier 78. This pocket 79, which may be provided with any of the embodiments of the present invention, may be useful in enhancing the emissions generated and transmitted to the photodiode 124 by a liquid phase (or layer) situated in the pocket 79 while the swabbing pad 54 is compressed.

As can be seen in FIGS. 10A through 11B, the swabbing pad 54 of the present invention may be formed in one of a number of shapes. These differing shapes may include a blunt or rounded end, as shown in FIGS. 10A and 11B, or a more pointed end as can be seen in FIG. 11A. Regardless of the shape of the swabbing pad employed, it is important that the openness or porosity of the swabbing pad 54 be such that when the first surface 54a of the swabbing pad 54 is brought into pressure contact with a suitably shaped porous pad 68, the swabbing pad is compressed, with the distance between at least one portion of the first surface 54a and the second surface 54b being substantially reduced by said pressure contacting. This will clearly result in a more complete wetting of the porous pad 68 and the transfer of wetting agent, analyte, and other materials to the support and reading pad 56.

The embodiments of the detector cap assemblies 30 through 30d, which are illustrated in FIGS. 5A through 11B, are exemplary of many such possible arrangements and structures. In addition, it must be understood that it is possible to provide yet other structures wherein the swabbing pad 54 and porous (reagent impregnated) pad 68 are reversed. That is, the swabbing pad 54 is removed from a detector assembly for swabbing of the test surface, while the porous pad (and possibly the support and reading pad 56) are positioned superposed over a photo detection means (of a suitable luminometer). The latter arrangement is not explicitly illustrated, but may be readily provided via this disclosure by skilled persons.

Figure 12:
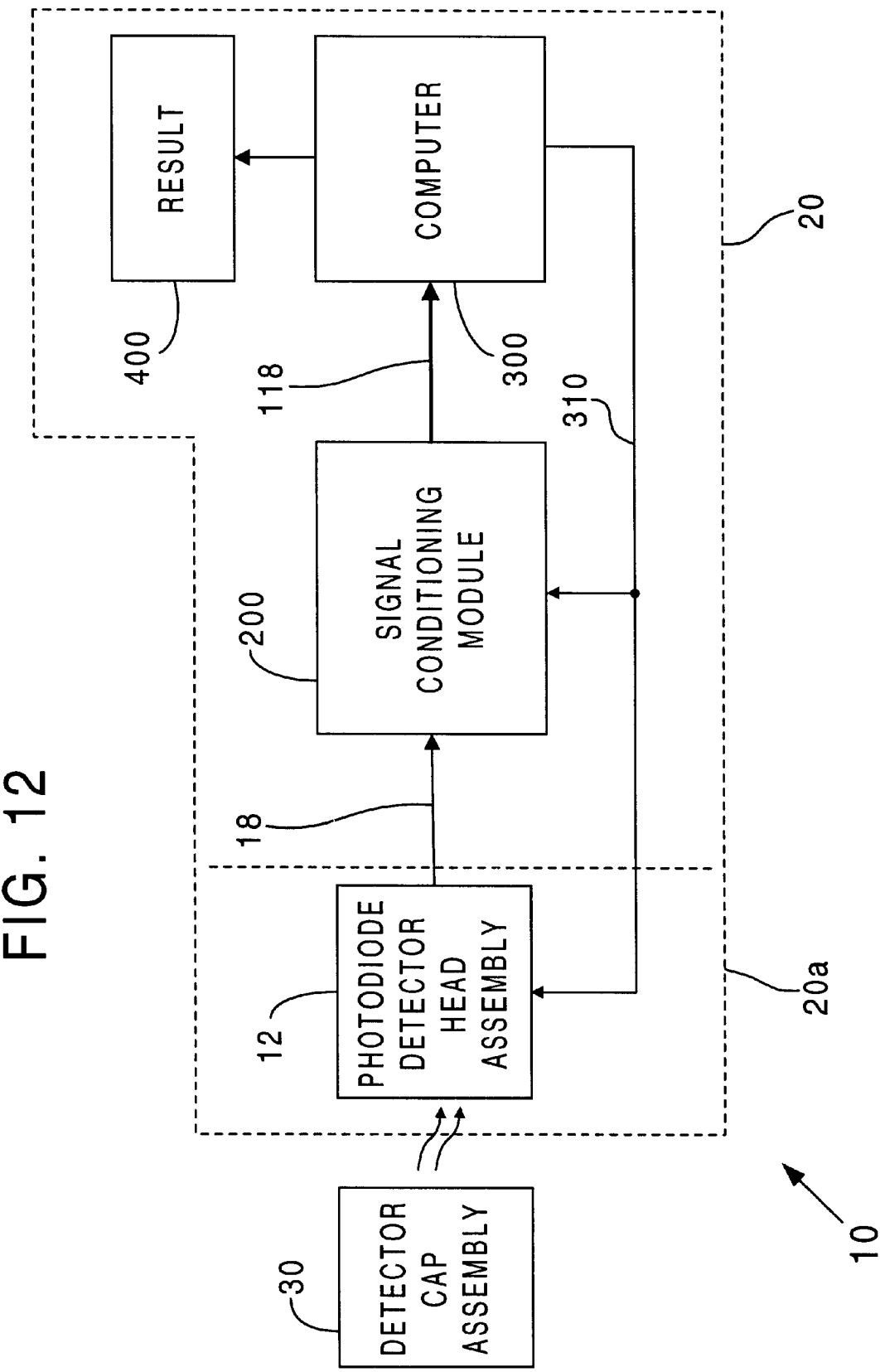
FIG. 12 provides a high-level block diagram representative of preferred embodiments of a low level luminometer.

Referring now to FIG. 12, there is provided a high-level block diagram of preferred embodiments of a sensitive luminometer 10 and assaying arrangement in accordance with the present invention. The detector cap assembly 30, as discussed above, is configured to be removably fixed to the photodiode detector head assembly 12. The photodiode detector head assembly 12 is structured to enable the detection of the light emissions produced by at least one of a bioluminescent and or a chemiluminescent assaying reaction. The detection is indicated by at least one electrical signal 18 representative of the detected luminescent emissions produced by a suitable assay reaction. The electrical signal 18 is generated by suitable solid-state photoelectronic and electronic circuits of the photodiode detector head assembly 12. In the most preferred embodiments the luminometer 10 is housed in a hand holdable housing 20. As such, the luminometer 10 of the present invention is highly portable and fully self-contained.

A portion of the housing 20, which is structured to suitably hold or accept the photodiode detector head assembly 12, is the detector head housing 20a. The detector head housing 20a is clearly illustrated in a preferred embodiment in FIG. 1 and FIG. 2. An important feature of the detector cap assembly 30 and the photodiode detector head assembly 12, is the placement of the source of the luminescent emissions very proximate to a photo detection means of the photodiode detector head assembly 12. This arrangement enables a source of low level emissions to be efficiently detected and quantified by the present invention. The electrical signal 18, which maybe comprised of several actual analog signals, is coupled to a signal conditioning module 200. The signal conditioning module 200 receives the electrical signal 18 from the photodiode detector head assembly 12, and conditions and processes the electrical signal 18 to produce at least one digital value 118 representative of the electrical signal 18 at one or more temporal instants during a pre-determined temporal interval. Accordingly, while the bioluminescent or chemiluminescent assaying reaction is occurring the electrical signal 18 is conditioned and processed by a suitable signal conditioning module 200 to produce one or more digital values 118 that are representative of the level or strength of the emissions detected at the temporal instants during the pre-determined interval. Skilled persons will appreciate that low level emissions may be best quantified by techniques that involve the 'integration' of such a low level signal over a suitable temporal interval. Further, such integration may be proved by analog circuitry, or alternately by digital means employing hardware and or software based counting and accumulation techniques.

As can be seen in FIG. 12, a computer 300 is included in the luminometer 10 to receive and process the digital values 118 produced by the signal conditioning module 200. The computer 300 may be programmed, therefore, to collect, accumulate, and or process one or more digital values 118 to enable a result 400, which may be termed a 'quantitative determination', to be generated that may be indicative of a level and possibly duration of the luminescent emissions detected by the detector head assembly 12. It should be noted that the signal conditioning module 200, the computer 300, and a means to provide the result 400 to a user are all contemplated in preferred embodiments as being housed within the housing 20. Further, the quantitative determination may be provided as a visual and or audible result.

It is important to note that the quantitative determination, say by way of result 400, may equivalently be termed a 'quantified result'. For example, assume the detected luminescent emissions are produced by a bioluminescent luciferase-luciferin assaying reaction. Then the quantified result may be indicative of a quantity of analyte that is associated with the emissions being produced. Further, the level of luminescent emissions detected and measured may be compared by the computer 300 to a pre-determined threshold level established to determine if a quantity of analyte associated with the bioluminescent assaying reaction is greater than a pre-determined quantitative limit. The pre-determined threshold level, which may be user selectable and or programmed into the computer 300, may be selected to indicate when a quantity of analyte associated with the bioluminescent assaying reaction is above an acceptable or safe limit. Accordingly, the quantitative result may simply provide a pass or fail indication. Skilled persons can provide other quantitative results that would be useful to a user or operator of the invention.

Figure 13:
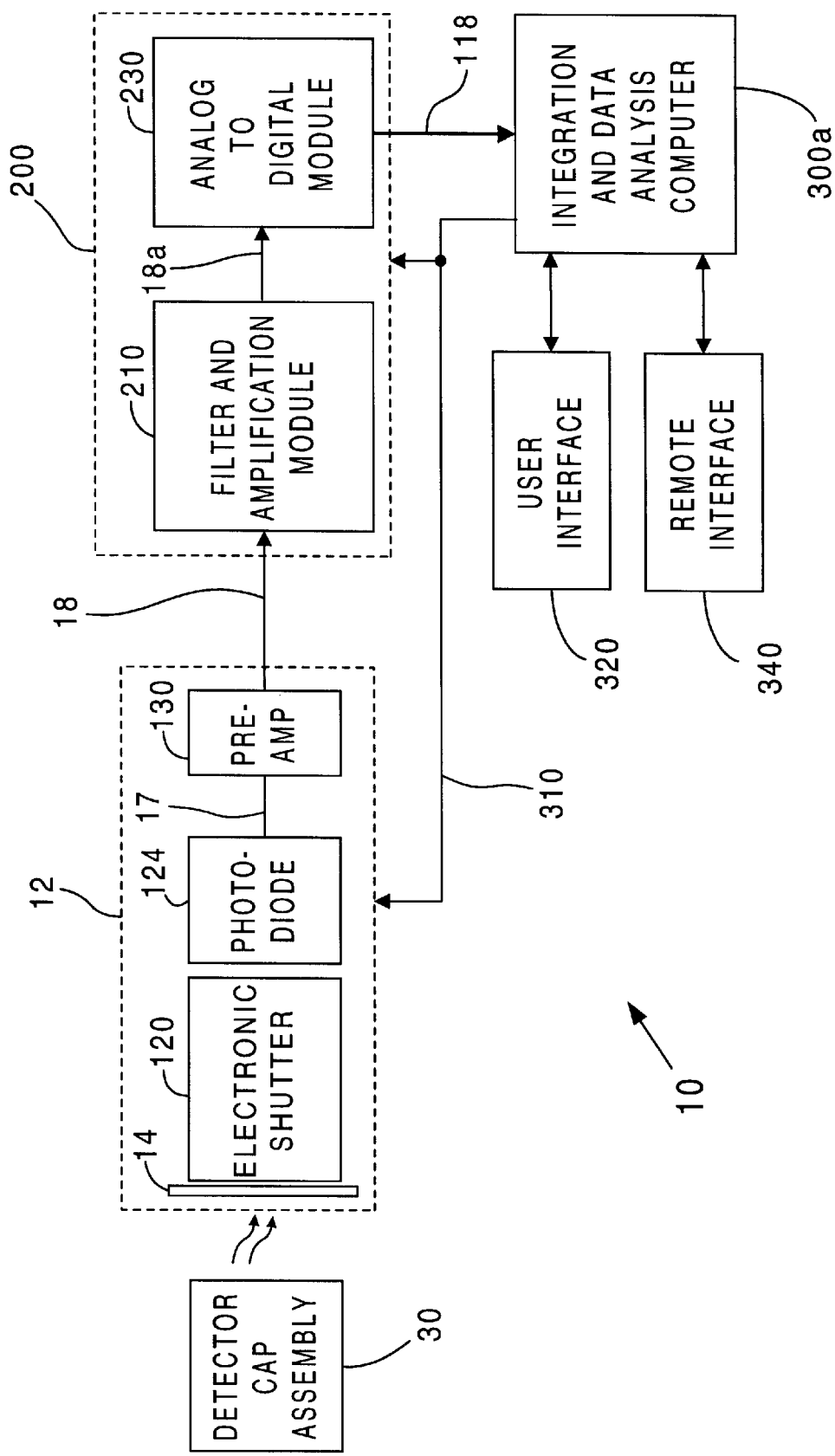
FIG. 13 is functional block diagram of a first embodiment of the luminometer.

Turning to FIG. 13, there is provided a more detailed block diagram of an embodiment of an assaying arrangement in accordance with the present invention. A first embodiment of the luminometer 10 includes a photodiode detector head assembly 12, a signal conditioning module 200, and an integration and data analysis computer 300a. As can be seen, the photodiode detector head assembly 12 may include an electronic shutter 120, a (semiconductor) photodiode 124, and a pre-amp 130. The photodiode 124 may be termed a 'semiconductor photodetector', or equivalently may comprise a portion of a 'photo detection means'. In a preferred embodiment of the luminometer 10 the photodiode 124 is provided by a semiconductor PIN photodiode detector. In a most preferred embodiment the photodiode 124 would be provided by a PIN photodiode 124a having a photo-detection surface area of 1–7 square milli-meters (mm) and preferably operated in a photo-voltaic mode. Accordingly, the photodiode 124 may be arranged to produce a current signal 17 that is proportional to the detected low level of luminescent emissions incident upon the photodiode. The pre-amplifier 130 is provided having an input and an output. The input of the pre-amplifier 130 is coupled to the photodiode 124 to receive the current signal 17. The output of the pre-amplifier 130 produces the electrical signal 18. As such, the pre-amplifier 130 provides a higher level signal to the signal conditioning module 200 than is produced by the photodiode 124. It should be understood that the photodiode 124 and the pre-amplifier 130 may most preferably be housed in a single electronic package. The most preferred physical arrangements of the electronic shutter 120, the photodiode 124 and the pre-amplifier 130 will be further addressed when referring to FIGS. 17A and 17B.

The photodiode detector head assembly 12 may include one or more electronic shutters 120 that are responsive to the computer 300a. The electronic shutter 120 is preferably superposed over and abutting the semiconductor photodiode 124 and immediately below or behind the transparent window 14 (also shown in FIGS. 2, 6A, etc.) of the photodiode detector head assembly 12. Importantly, the window 14 is the only avenue for luminescent emissions to be incident upon and detected by the photodiode 124. The electronic shutter 120 is configured to be set to one of either a darkened state thereby significantly restricting the level of luminescent emissions incident upon the photodiode 124 and a nearly transparent state enabling available luminescent emissions to reach and be detected by the photodiode 124. The term 'significantly restricting', as applied to the level of emissions reaching the photodiode 124 when the electronic shutter 120 is in the darkened state, may be assumed to indicate that the level of emissions reaching and detected by the photodiode 124 may be reduced to a level of ¹/₂₀₀th to ¹/₄₀₀th of the level incident when the electronic shutter 120 is in the nearly transparent state. The capability to significantly reduce the level of emissions reaching the photodiode 124 is desirable for a number of reasons. First, as the luminometer 10 of the invention is constructed to be sensitive to low levels of emissions, exposure to the relatively high levels of common ambient room lighting may saturate or even damage the electronic circuits of the luminometer 10. Accordingly, when the detector cap assembly is not installed over the photodiode detector head assembly 12 (or the second portion 40 is removed from the first portion 32), it is desirable to have the computer 300a set the electronic shutter 120 to the darkened state. Other functions of the electronic shutter 120, which will be fully discussed below, include determining levels of dark noise prior to and or during assaying measurements and activities involving the use of the luminometer 10.

Although mechanical shutters may be employed with the present invention, the use of electronic shutters 120 reduces the mechanical complexity and the cost of construction for preferred embodiments of the photodiode detector head assembly 12. As skilled persons will appreciate, a most preferred version of the electronic shutter 120 may be provided by a polarizing liquid crystal shutter, also known as a LCD shutter. By including control bus 310 of FIGS. 13 through 15, the computer 300 can vary settings associated with, for example, the photodiode detector head assembly 12 and the signal conditioning module 200.

Referring again to FIG. 13, an embodiment of the signal conditioning module 200 is provided that may include a filter and amplification module 210 that receives the electrical signal 18 at its input and processes it by filtering and or amplifying the signal. The processing, which is providable by analog circuitry, may limit the bandwidth of the electrical signal 18 to minimize the noise associated with the detected luminescent emissions. A processed version of the electrical signal 18a is then coupled via an output of the filter and amplification module 210 to an analog-to-digital module 230 for conversion to representative digital values. The digital values 118 are then collected and processed by the computer 300a. The digital values 118 may be provided to the computer 300a by known parallel or serial digital transfer techniques. Once processing by the computer 300a is complete, a user interface 320 may be employed to indicate the (quantified) result 400 to a user or operator. The presented result may simply be a 'pass/fail' indication, a result calibrated in user friendly weighted scale, and or a result indicating the number of moles of analyte detected.

Figure 14:
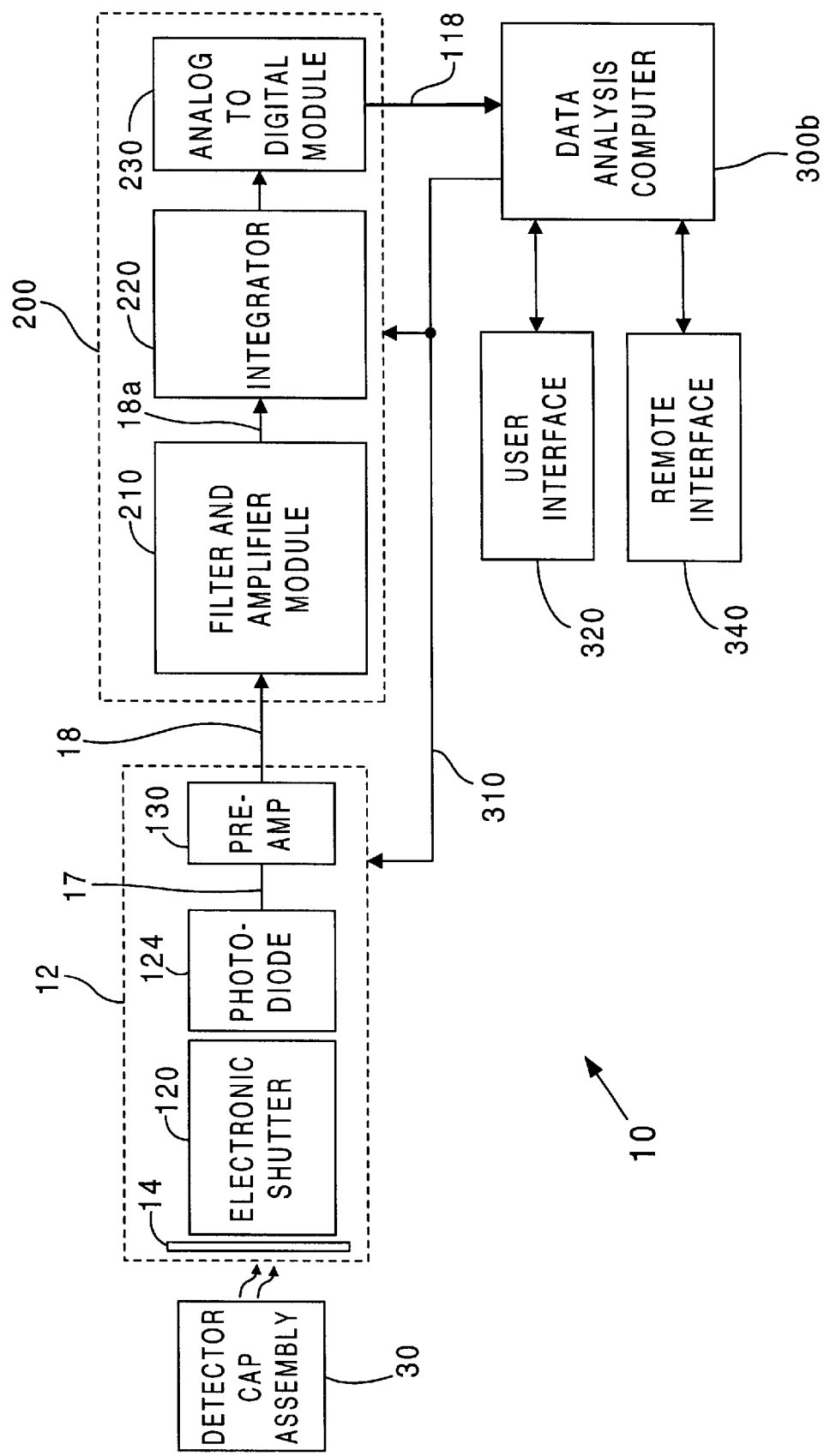
FIG. 14 is functional block diagram of another embodiment of the luminometer.

As clearly shown in FIG. 14, the signal conditioning module 200 may be modified to explicitly include an integrator 220 that is interposed between the filter and amplification module 210 and the analog-to-digital module 230. The integrator 220 includes integration circuitry provided to integrate a signal provided by the output of the filter and amplification module and produce an integrated output signal indicative of a total amount luminescent emissions detected over at least one portion of the pre-determined temporal interval. Accordingly, integration module 220 integrates the electrical signal 18a over a temporal interval and ultimately provides an accumulated value or total to a data analysis computer 300b. A application program or other suitable software of the computer 300b, may now omit the functions provided to integrate the digital values 118 as the integration function is now provided in the hardware of the integrator 220.

The user interface 320, which may be arranged as depicted in FIG. 1, is operatively coupled to an included computing means (e.g., computer 300 or 300a) and is configured to enable information to be exchanged with the user. The information exchanged may enable the user to realize or accomplish a number of actions including the inputting of gain settings to the luminometer, the calibrating of the luminometer to perform a measurement of a level of luminescent emissions associated with an assaying reaction, reset the luminometer after one measurement has been completed and before another is to begin, establish the duration of the pre-determined temporal interval during which the luminescent emissions are to be detected and measured, select one of a plurality of specific pre-determined threshold levels to be associated with a level of luminescent emissions to be determined during a respective pre-determined temporal interval, determine the power level of at least one internal rechargeable battery included within the housing, and power on and off the luminometer. In addition to the user interface 320, a remote interface 340 may be included to enable information be sent to and received from the luminometer 10/10a. The remote interface may include the optical port 22, which is shown in FIG. 1. As such, the optical port 22 may be employed to enable an optical link to be established between the luminometer 10/10a and another instrument (such as a suitably configured personal or portable computer).

Figure 15:
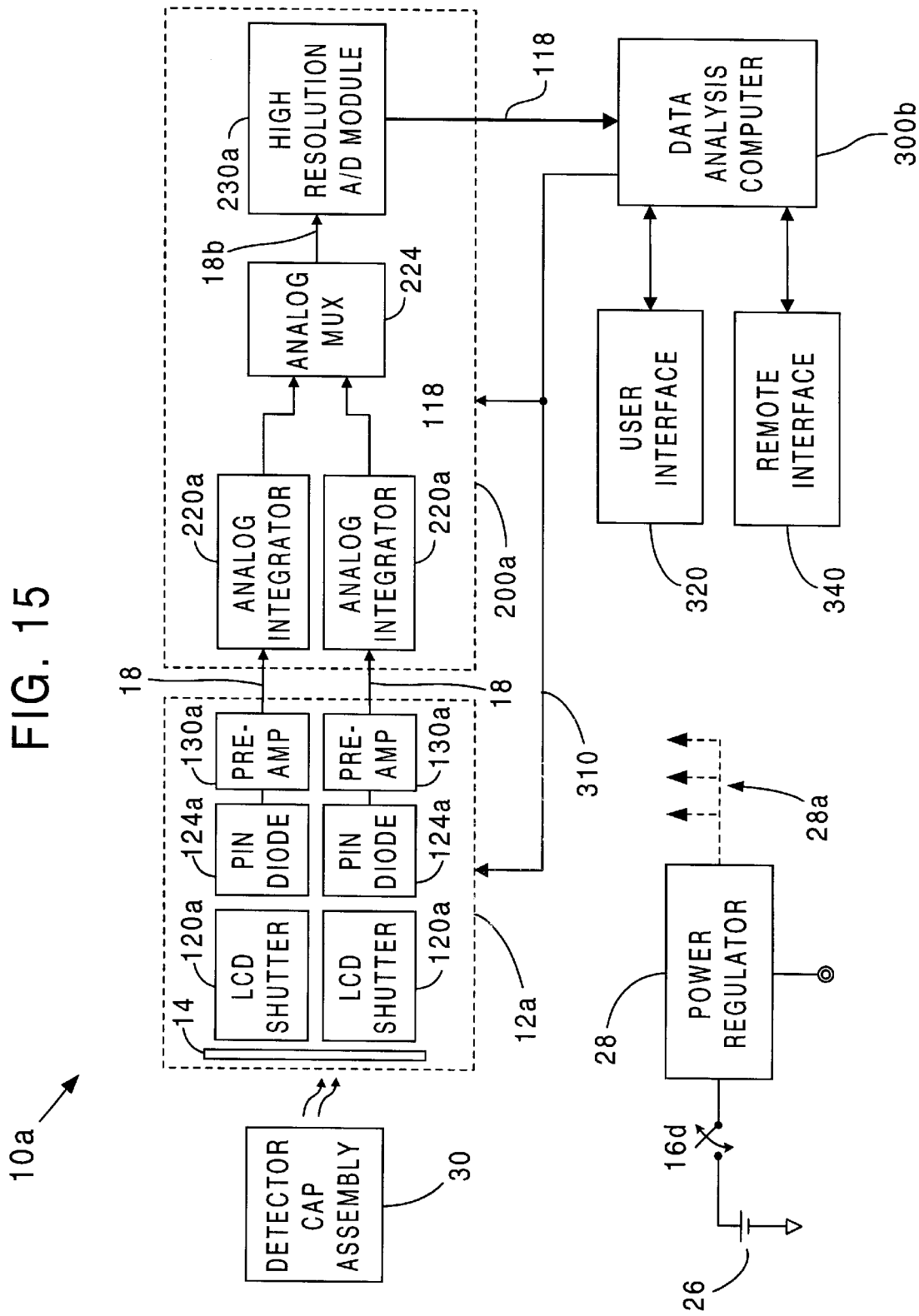
FIG. 15 provides a functional block diagram of a preferred embodiment of a multi-channel low level luminometer of the present invention.

Turning now to FIG. 15, there :is illustrated a possibly most preferred embodiment of the luminometer 10 of the present invention. As illustrated, a multi-channel embodiment includes a photodiode detector head assembly 12a. The photodiode detector head assembly 12a is structured having a plurality of photodiodes and electronic shutter 120s. As shown, each LCD shutter 120a is arranged to cause a significant restriction in the level of luminescent emissions that may reach each respective photodiode. The photodiodes are most preferably provided by PIN photodiodes 124a. A signal conditioning module 200a, which may be termed a signal conditioning means, is operatively coupled to the photodiode detector head assembly 12a to receive, condition, and process each of a possible plurality of the electrical signals 18. As above the electrical signals 18 are processed to produce a sequence of digital values 118 representative of the electrical signals 18 over a pre-determined temporal interval. The digital values 118 may be coupled to a high resolution analog-to-digital module 230a via an analog multiplexer 224. The term 'high resolution' is intended to indicate that the analog-to-digital module 230a employed provides digital values 118 with a sufficient number of bits of resolution. For example, preferred embodiments of analog-to-digital module 230a may provide 18 to 20 bits of resolution. As with the embodiment of FIG. 14, a computing means may be provided such as computer 300b. The computer 300b would again be coupled to the signal conditioning module 200a to collect and process the sequence of digital values 118 to enable the quantified result to be generated and delivered to a user or operator.

As skilled persons will appreciate, alternate embodiments of the multi-channel arrangement provided in FIG. 15 are certainly possible. For example, the analog multiplexer 224 may be moved to receive the signals 18 from the photodiode detector head assembly 12a, resulting in the need for only a single analog integrator 220a. Other variations are certainly possible and are considered within the scope of the present invention. It is important to understand that the system structure of FIG. 15, enables a first signal that has been sampled for a pre-determined temporal sub interval to be converted-by the high resolution a/d module 230a, while a second signal (say from another photo detection means) is being integrated.

The operation of the luminometers 10/10a of FIGS. 12 through 15 may be provided by a number of suitable algorithms. For example, when considering the embodiment of FIG. 13 when only one photodiode 124 is provided, it may be necessary to calibrate the luminometer 10 when the source of luminescent emissions is not active (i.e., a reaction is not occurring), possibly with the electronic shutter 120 in the darkened state. Subsequently, the assaying reaction may be started (with a suitable indication directly or indirectly provided to the computer 300a). The electronic shutter 120 would be set to the near transparent state, and the luminescent emissions from said assaying reaction would be detected and measured. An alternate measurement algorithm, which may be employed if the assaying reaction is of a sufficient temporal duration, may be summarized as follows. A series of alternating measurements of a dark signal noise level (taken with the electronic shutter 120 in the darkened state) may be collected in an interleaved fashion with measurements of the level of luminescent emissions (taken with the electronic shutter 120 in the transparent state). A system that collects a series of dark noise values and a series of actual luminescent emission values, may employ known signal processing relationships that will enable accurate measurements to be made and may enable the effects of noise changes and circuit related drifting to be greatly reduced and or eliminated.

When considering the embodiment of FIG. 15, the presence of two or more photo-channels, say with each having an electronically controlled LCD shutter 120a, enables the overlapping of measurements to be made of the dark current noise level and the level of luminescent emissions associated with the measured bioluminescent and or chemiluminescent assaying reaction. That is, a first analog integrator 220a may be integrating one signal, while an output of a second analog integrator is sampled and converted to a digital value 118. This structure enables the overlap of the integration activities with the conversion and collecting activities.

Figure 17A:
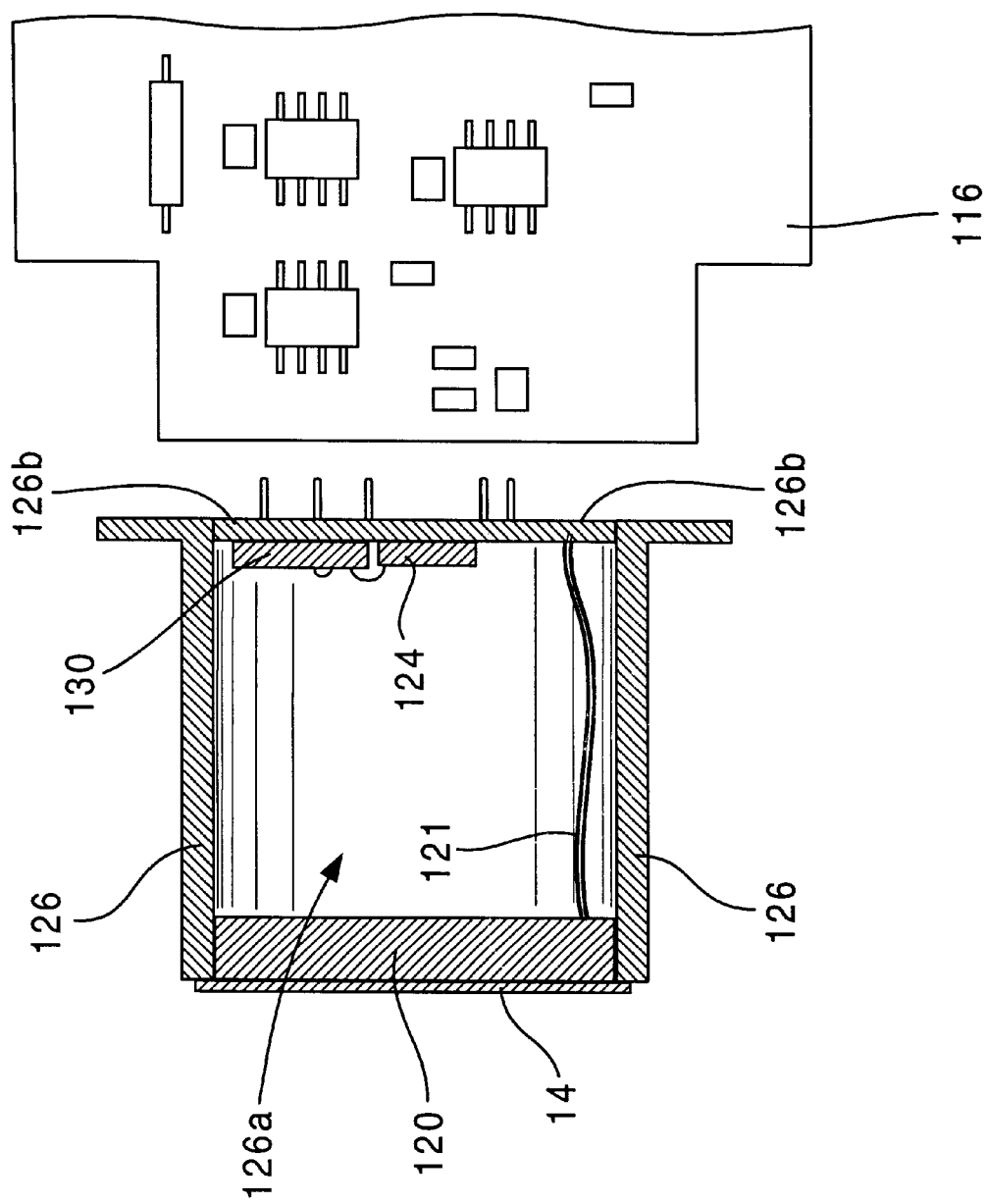

Turning now to FIG. 16, there is illustrated a preferred embodiment of the photodiode detector head assembly 12. As shown, an arrangement is provided having the PIN photodiode 124a (with a window thereof) abutting and superposed by an electronic shutter 120, possibly further including a transparent window 14. A circuit board 116 may be included to provide the required electronic modules including the signal conditioning module 200, among others. As discussed above, this arrangement of components provides a photodiode detector head assembly 12 that places a photo detection means, such as a PIN photodiode 124a, in close proximity to a source of luminescent emissions. Ideally, the source of emissions would be placed superposed to and possibly abutting the left side of the transparent window 14 (as seen in FIG. 6A). A most preferred arrangement of a photodiode detector head assembly may be provided by including a more integrated photo detection means as shown in FIG. 17A. As depicted therein, a photodetector package 126 is structured to house a photodiode 124 and a pre-amplifier 130 within a chamber 126a. The photodiode 124 and pre-amplifier 130 are preferably fixed to a base 126b of the photodetector package 126. An electronic shutter 120 may be provided in place of the standard optical window of a typical photo detection means. The arrangement of the electronic shutter 120 fixed to and mounted on the photodetector package 126 enables a distance between the photodiode 124 and a source of luminescent emissions to be reduced accordingly. Therefore, as skilled persons would appreciate, the structure depicted in FIGS. 17A and 17B, may be advantageous to the arrangement of FIG. 16. Further, it should be understood that the distance between the electronic shutter 120 and the photodiode 124, as depicted in FIGS. 17A and 17B, is illustrative only and may certainly be reduced.

As can be seen in FIG. 17B, a thermoelectric cooler 128 may be mounted within the chamber 126a to enable the photodiode 124 and or the pre-amplifier 130 to be cooled to a suitable operating temperature. As skilled persons will understand, thermoelectric cooling elements are often employed to reduce the noise level of electronic devices and circuits. The window 14, which as depicted in FIG. 17B in a modified embodiment 14a, may be included as part of the photodetector package 126, if necessary. As shown in FIG. 17B, the window 14a may be structured to provide the function of an optical lens.

In order to not obfuscate the essential functional and operational characteristics of the various embodiments of the invention as illustrated, certain items have been omitted. For example in FIGS. 12 through 14, the inclusion of a power source, such as a (rechargeable) battery and a power regulator, have been omitted. These items, or equivalents thereof, which have been depicted in FIG. 15, may be termed an 'internal power supply', and would typically include a battery 26 and a power regulator 28. One or more power providing output coupling lines 28a may be included to couple operating (e.g., bias), power to the various components of the invention. Therefore, it should be noted that an internal power supply would certainly be required with any of the disclosed preferred, self-contained, and hand holdable embodiments of the luminometer 10/10a of the present invention. Yet other well known items not shown or discussed, may certainly provided by skilled persons, as required. For example, when considering FIGS. 1 through 10B, the use of threading and or bayonet mounting arrangements may be employed with the various embodiments of items that are contemplated to be removably fixed to at least one other item. Such items may include the first portion 32, the second portion 40/40', and the detector head housing 20a. As such, the presently provided descriptions are intended to broadly define the invention, and not necessarily be constrained to the explicit embodiments illustrated.

While there have been described a plurality of the currently preferred embodiments of the present invention, along with varied methods of operation, those skilled in the art will recognize that other and further modifications may be made without departing from the invention, and it is intended to claim all modifications and variations as fall within the scope of the described invention and the appended claims.

What is claimed is:

1. A swabbing structure for use in swabbing a test surface in order to collect and support a quantitative determination of the presence of collected analyte, the swabbing structure comprising:

a) a pre-wetted swabbing pad having a first surface and a second surface, the first surface configured for contacting the test surface to collect available analyte located thereupon;

b) a substantially flattened support and reading pad having a first side fixed to the second surface of the swabbing pad, the first side of the support and reading pad substantially superposed by the second surface of the swabbing pad;

c) means to support the support and reading pad, and therefore the swabbing pad, to enable swabbing of the test surface and subsequently facilitate the detecting, in a light-tight environment, of any low level luminescent emissions emitted from a second side of the support and reading pad; and d) a movable structure having a porous pad fixed thereto, the porous pad impregnated with dried reagents, with the movable structure configured to bring the porous pad into pressure contact in the light-tight environment with the first surface of the pre-wetted swabbing pad, compressing the swabbing pad, and causing the wetting and activating of the dried reagents of the porous pad, and further drawing the reagents to the swabbing pad, possibly resulting in an assaying reaction that produces the low level luminescent emissions, which are detectable and quantifiable from the second side of the support and reading pad of the swabbing structure.

2. The swabbing structure in accordance with claim 1, wherein the support and reading pad has a porosity in the range of 60 to 95 percent and will readily absorb fluid from the swabbing pad and porous pad, when the swabbing and porous pads are brought into pressure contact.

3. The swabbing structure in accordance with claim 2, wherein the support and reading pad and the swabbing pad are embodied in a bright, reflective color, enabling any low level luminescent emissions produced by the assaying reaction to be detected by at least one of:

(a) detecting direct emissions produced at or near the second side of the support and reading pad;

(b) detecting reflected luminescent emissions that are transmitted by the reflective porosity of the swabbing pad, the porous pad, and the support and reading pad; and (c) detecting luminescent emissions that are transmitted through and produced within a liquid phase situated between the second side of the support and reading pad and a transparent second barrier of the swabbing structure, with the transparent second barrier substantially superposing the second side of the support and reading pad.

4. The swabbing structure in accordance with claim 3, wherein the swabbing pad and the support and reading pad are each constructed of a porous polymer material.

5. The swabbing structure in accordance with claim 4, wherein the swabbing structure is configured to be removably fixed to a means to detect and quantify the low level luminescent emissions when the swabbing pad is brought into pressure contact with the porous pad, assuming sufficient quantities of analyte have been collected upon the first surface of the swabbing pad by the swabbing of the test surface.

6. The swabbing structure in accordance with claim 5, wherein said means to detect and quantify the low level luminescent emissions includes a photodiode placed proximate to the second side of the support and reading pad to enable efficient detecting of any low level luminescent emissions being emitted therefrom.

7. A method of swabbing a test surface in order to collect and indicate the presence of an analyte, the method comprising the steps of:

a) swabbing the test surface with a pre-wetted swabbing pad, wherein the pre-wetted swabbing pad is structured having a first surface and a second surface, with the first surface shaped and configured for contacting the test surface to collect therefrom available analyte;

b) forming a light-tight environment, with the swabbing pad contained within the light-tight environment;

c) bringing the first surface of the swabbing pad into pressure contact with dried reagents possibly causing a detectable low level luminescent reaction, within the light-tight environment, if sufficient analyte has been collected by the swabbing of the test surface; and d) efficiently detecting and quantifying low level luminescent emissions, if produced within the light-tight environment at a detectable intensity.

8. The method in accordance with claim 7, wherein the step of bringing the first surface of the swabbing pad into pressure contact with the dried reagents is realized by employing dried reagents impregnated into a porous pad, with the porous pad compressing the swabbing pad causing an activating of the dried reagents, and further causing a reduction in a distance between at least one portion of the first surface of the swabbing pad and the second surface thereof, enabling a more efficient detecting of any emitted low level luminescent emissions by a detection means efficiently positioned proximate to the second surface of the swabbing pad.

9. A method of collecting analyte from a test surface and quantitatively indicating the presence of said analyte, the method comprising the steps of:

a) swabbing the test surface with a pre-wetted swabbing pad employing a first surface of the swabbing pad for contacting the test surface to collect available analyte;

b) bringing the first surface of the swabbing pad into pressure contact with dried reagents, within a darkened light-tight environment, causing a compressing of the swabbing pad and possibly causing a detectable low-level luminescent reaction to commence; and (c) detecting and quantifying, in the darkened light-tight environment, low level luminescent emissions emitted, at least in part, from the swabbing pad.

10. The method in accordance with claim 9, wherein the step of detecting and quantifying the low level luminescent emissions involves sensing luminescent emissions emitted from a second surface of the swabbing pad.

11. The method in accordance with claim 10, wherein the step of bringing the first surface of the swabbing pad into pressure contact with dried reagents involves the use of a porous pad having the dried reagents impregnated therein, with the porous pad brought into pressure contact with the first surface of the swabbing pad.

12. The method in accordance with claim 11, wherein the step of bringing the first surface of the swabbing pad into pressure contact with dried reagents involves a compressing of the swabbing pad such that the first surface and a second surface of the swabbing pad are compressed with the distance between at least one portion of the first surface and the second surface being substantially reduced with the pressure contacting of the porous pad and the swabbing pad, enabling a more efficient detection of any emitted low level luminescent emissions.

13. The method in accordance with claim 12, wherein the step of swabbing the test surface with a pre-wetted swabbing pad involves the use of a swabbing pad that is supported upon a substantially flattened support and reading pad that is interposed between the second surface of the swabbing pad and a detection means, with a first side of the support and reading pad fixed to, and substantially superposed by the second surface of the swabbing pad.

* * * * *